US011268056B2

(12) United States Patent
Norderhaugh et al.

(10) Patent No.: US 11,268,056 B2
(45) Date of Patent: Mar. 8, 2022

(54) FLEXIBLE BIOPROCESSING CONTAINER WITH PARTIAL DIVIDING PARTITION

(71) Applicants: LIFE TECHNOLOGIES CORPORATION, Carlsbad, CA (US); LIFE TECHNOLOGICES AG, Oslo (NO)

(72) Inventors: Lars Norderhaugh, Nesoddtangen (NO); Angel Varela-Rohena, Carlsbad, CA (US); Nephi D. Jones, Netwon, UT (US)

(73) Assignees: Life Technologies Corporation, Carlsbad, CA (US); Life Technologies AS, Oslo (NO)

( * ) Notice: Subject to any disclaimer, the term of this patent is extended or adjusted under 35 U.S.C. 154(b) by 542 days.

(21) Appl. No.: 16/067,495

(22) PCT Filed: Dec. 21, 2016

(86) PCT No.: PCT/US2016/068067
§ 371 (c)(1),
(2) Date: Jun. 29, 2018

(87) PCT Pub. No.: WO2017/116910
PCT Pub. Date: Jul. 6, 2017

(65) Prior Publication Data
US 2019/0010435 A1 Jan. 10, 2019

Related U.S. Application Data

(60) Provisional application No. 62/272,585, filed on Dec. 29, 2015.

(51) Int. Cl.
*C12M 1/26* (2006.01)
*B03C 1/30* (2006.01)
(Continued)

(52) U.S. Cl.
CPC .......... *C12M 1/266* (2013.01); *A61M 1/3618* (2014.02); *B01L 3/505* (2013.01);
(Continued)

(58) Field of Classification Search
None
See application file for complete search history.

(56) References Cited

U.S. PATENT DOCUMENTS 3,140,716 A 7/1964 Harrison et al.
3,212,274 A 10/1965 Eidus
(Continued)

FOREIGN PATENT DOCUMENTS

CN 2642387 Y 9/2004
CN 1649654 A 8/2005
(Continued)

OTHER PUBLICATIONS

International Search Report and Written Opinion dated Apr. 3, 2017, issued in PCT Application No. PCT/US2016/068067, filed Dec. 21, 2016.
(Continued)

*Primary Examiner* — David C Mellon
(74) *Attorney, Agent, or Firm* — Workman Nydegger

(57) ABSTRACT

Methods of separating magnetic particles from a fluid include introducing a fluid mixture that includes a liquid media, a biological component, and magnetic particles into an internal compartment of a container through an inlet, allowing at least a portion of the mixture to travel around a partition formed within the internal compartment and then exit the internal compartment through an outlet on the opposite side of the partition, and applying a magnetic field to the mixture in the internal compartment so that the magnetic particles are retained within the container or internal compartment thereof by the magnetic field. The
(Continued)

partition is formed by permanently or reversibly securing upper and lower container walls together, such as by welding or pressing, between the inlet and the outlet such that the media and biological component must flow around the partition and through the magnetic field to exit the internal compartment through the outlet.

22 Claims, 10 Drawing Sheets

(51) Int. Cl.

| | | |
|---|---|---|
| *B03C 1/01* | (2006.01) | |
| *B03C 1/28* | (2006.01) | |
| *A61M 1/36* | (2006.01) | |
| *B01L 3/00* | (2006.01) | |
| *C12M 3/00* | (2006.01) | |
| *C12M 1/00* | (2006.01) | |
| *C12M 1/12* | (2006.01) | |
| *C07K 16/28* | (2006.01) | |

(52) U.S. Cl.
CPC .............. *B03C 1/01* (2013.01); *B03C 1/288* (2013.01); *B03C 1/30* (2013.01); *C12M 3/00* (2013.01); *C12M 23/14* (2013.01); *C12M 23/26* (2013.01); *C12M 37/04* (2013.01); *B01L 2200/0647* (2013.01); *B01L 2200/0668* (2013.01); *B01L 2400/043* (2013.01); *B03C 2201/18* (2013.01); *B03C 2201/26* (2013.01); *C07K 16/2809* (2013.01); *C07K 16/2818* (2013.01)

(56) References Cited

U.S. PATENT DOCUMENTS

| | | |
|---|---|---|
| 3,221,724 A | 12/1965 | Wentworth |
| 3,304,977 A | 2/1967 | Hammons |
| 3,422,887 A | 1/1969 | Berkeley |
| 3,672,959 A | 6/1972 | Sweet |
| 3,690,045 A | 9/1972 | Neumann |
| 3,867,260 A | 2/1975 | Freedman |
| 4,112,829 A | 9/1978 | Poinsard |
| 4,177,816 A | 12/1979 | Torgeson |
| 4,182,656 A | 1/1980 | Ahnell et al. |
| 4,194,950 A | 3/1980 | Zalles |
| 4,197,098 A | 4/1980 | Stiehl |
| 4,258,784 A | 3/1981 | Perry et al. |
| 4,309,592 A | 1/1982 | Le Boeuf |
| 4,561,498 A | 12/1985 | Nowobilski et al. |
| 4,573,933 A | 3/1986 | Camron |
| 4,574,876 A | 3/1986 | Aid |
| 4,612,086 A | 9/1986 | Dominguez |
| 4,668,388 A | 5/1987 | Dibble et al. |
| 4,731,072 A | 3/1988 | Aid |
| 4,744,414 A | 5/1988 | Schon |
| 4,797,587 A | 1/1989 | Tschudi et al. |
| 4,863,452 A | 9/1989 | Irmiter et al. |
| 4,910,148 A | 3/1990 | Sorensen et al. |
| 4,935,134 A | 6/1990 | Hensgen |
| 5,121,857 A | 6/1992 | Hutchinson |
| 5,243,833 A | 9/1993 | Coelho et al. |
| 5,245,693 A | 9/1993 | Ford et al. |
| 5,271,557 A | 12/1993 | Lynch et al. |
| 5,287,918 A | 2/1994 | Banks et al. |
| 5,306,269 A | 4/1994 | Lewis et al. |
| 5,350,513 A | 9/1994 | Markowitz |
| 5,372,621 A | 12/1994 | Staton |
| 5,381,510 A | 1/1995 | Ford et al. |
| 5,411,077 A | 5/1995 | Tousignant |
| 5,417,729 A | 5/1995 | Greenleaf, Sr. |
| 5,443,985 A | 8/1995 | Lu et al. |
| 5,512,141 A | 4/1996 | Koistinen et al. |
| 5,536,475 A | 7/1996 | Moubayed et al. |
| 5,632,793 A | 5/1997 | Haggard |
| 5,691,208 A * | 11/1997 | Miltenyi ............. A61M 1/3603 436/526 |
| 5,875,282 A | 2/1999 | Jordan et al. |
| 5,885,453 A | 3/1999 | Chatelin et al. |
| 6,003,593 A | 12/1999 | Halligan |
| 6,083,587 A | 7/2000 | Smith et al. |
| 6,126,835 A | 10/2000 | Barbera-Guillem et al. |
| 6,133,021 A | 10/2000 | Gu et al. |
| 6,165,105 A | 12/2000 | Boutellier et al. |
| 6,391,093 B1 | 5/2002 | French |
| 6,409,785 B1 | 6/2002 | Smithies et al. |
| 6,432,698 B1 | 8/2002 | Gaugler et al. |
| 6,490,824 B1 | 12/2002 | Maekawa et al. |
| 6,535,689 B2 | 3/2003 | Augustine et al. |
| 6,619,054 B1 | 9/2003 | Cargnelli et al. |
| 6,626,983 B1 | 9/2003 | Cairns |
| 6,673,098 B1 | 1/2004 | Machold et al. |
| 6,673,598 B1 | 1/2004 | Akers et al. |
| 6,882,797 B2 | 4/2005 | Stewart et al. |
| 7,004,196 B2 | 2/2006 | Schubmehl et al. |
| 7,011,797 B2 | 3/2006 | Bakke |
| 7,232,457 B2 | 6/2007 | Schmidt et al. |
| 7,235,402 B2 | 6/2007 | Aubry |
| 7,289,724 B2 | 10/2007 | Furnrohr et al. |
| 7,384,783 B2 | 6/2008 | Kunas et al. |
| 7,394,976 B2 | 7/2008 | Entenman et al. |
| 7,487,688 B2 | 2/2009 | Goodwin |
| 7,629,167 B2 | 12/2009 | Hodge et al. |
| 7,682,067 B2 | 3/2010 | West et al. |
| 7,722,839 B2 | 5/2010 | Kuzyk |
| 7,748,438 B2 | 7/2010 | Ghelli et al. |
| 7,819,934 B2 | 10/2010 | Galliher |
| 7,831,318 B2 | 11/2010 | Bartee et al. |
| 7,878,099 B2 | 2/2011 | Loibl |
| 7,879,599 B2 | 2/2011 | Goodwin et al. |
| 7,932,078 B2 | 4/2011 | Possemé et al. |
| 8,381,780 B2 | 2/2013 | Fisher et al. |
| 8,455,242 B2 | 6/2013 | Staheli et al. |
| 8,506,198 B2 | 8/2013 | West et al. |
| 8,603,805 B2 | 12/2013 | Goodwin et al. |
| 8,623,640 B2 | 1/2014 | Kunas et al. |
| 8,641,314 B2 | 2/2014 | Thacker et al. |
| 9,457,306 B2 | 10/2016 | Jones et al. |
| 2001/0024820 A1 | 9/2001 | Mastromatteo et al. |
| 2001/0039692 A1 | 11/2001 | Wright et al. |
| 2002/0131654 A1 | 9/2002 | Smith et al. |
| 2003/0077466 A1 | 4/2003 | Smith et al. |
| 2003/0106294 A1 | 6/2003 | Chung et al. |
| 2004/0062140 A1 | 4/2004 | Cadogan et al. |
| 2004/0149127 A1 | 8/2004 | Lyons |
| 2004/0209331 A1 | 10/2004 | Ririe |
| 2005/0239198 A1 | 10/2005 | Kunas et al. |
| 2005/0272146 A1 | 12/2005 | Hodge et al. |
| 2005/0287660 A1 | 12/2005 | Aubry |
| 2006/0196501 A1 | 9/2006 | Bibbo et al. |
| 2006/0240546 A1 | 10/2006 | Goodwin et al. |
| 2006/0270036 A1 | 11/2006 | Goodwin et al. |
| 2006/0275894 A1 | 12/2006 | Felder et al. |
| 2006/0279167 A1 | 12/2006 | Turner |
| 2007/0175831 A1 | 8/2007 | Almaasbak et al. |
| 2007/0199890 A1 | 8/2007 | Trogolo |
| 2007/0275452 A1 | 11/2007 | Yamasaki et al. |
| 2008/0060216 A1 | 3/2008 | Reilly |
| 2008/0068920 A1 | 3/2008 | Galliher et al. |
| 2008/0127832 A1 | 6/2008 | Zhang |
| 2008/0160591 A1 | 7/2008 | Willson et al. |
| 2008/0272146 A1 | 12/2008 | Hodge et al. |
| 2009/0035856 A1 | 2/2009 | Galliher et al. |
| 2009/0081742 A1 | 3/2009 | Dunlop et al. |
| 2009/0087903 A1 | 4/2009 | Belgrader et al. |
| 2009/0119869 A1 | 5/2009 | Yoo |
| 2009/0148143 A9 | 6/2009 | Entenman et al. |
| 2009/0233334 A1 | 9/2009 | Hildinger et al. |
| 2010/0075405 A1 | 3/2010 | Broadley et al. |
| 2010/0124564 A1 | 5/2010 | Martinson et al. |
| 2010/0151558 A1 | 6/2010 | Alianell et al. |
| 2010/0170400 A1 | 7/2010 | van den Boogard et al. |

(56) References Cited

U.S. PATENT DOCUMENTS

| | | |
|---|---|---|
| 2010/0229296 A1 | 9/2010 | Samuel |
| 2010/0237009 A1 | 9/2010 | Horst |
| 2010/0248333 A1 | 9/2010 | Bartilson |
| 2011/0046551 A1 | 2/2011 | Augustine et al. |
| 2011/0076759 A1 | 3/2011 | Reif et al. |
| 2011/0124087 A1 | 5/2011 | Meiser et al. |
| 2011/0188928 A1 | 8/2011 | West et al. |
| 2011/0198066 A1 | 8/2011 | Starbard |
| 2011/0198286 A1 | 8/2011 | Niazi |
| 2011/0207170 A1 | 8/2011 | Niazi |
| 2011/0207218 A1 | 8/2011 | Staheli et al. |
| 2011/0258975 A1 | 10/2011 | Lundgren |
| 2011/0310696 A1 | 12/2011 | Goodwin et al. |
| 2012/0094785 A1 | 4/2012 | Cheng et al. |
| 2012/0132548 A1 | 5/2012 | Galliher et al. |
| 2012/0177533 A1 | 7/2012 | Lee et al. |
| 2012/0260671 A1 | 10/2012 | Damren et al. |
| 2013/0082410 A1 | 4/2013 | Goodwin et al. |
| 2013/0089925 A1 | 4/2013 | Damren et al. |
| 2013/0101982 A1 | 4/2013 | Goodwin et al. |
| 2013/0260463 A1 | 10/2013 | Staheli et al. |
| 2014/0106453 A1 | 4/2014 | Kunas et al. |
| 2014/0251322 A1 | 9/2014 | Miller |
| 2014/0298612 A1 | 10/2014 | Williams et al. |
| 2015/0265943 A1 | 9/2015 | Brown et al. |
| 2015/0265958 A1 | 9/2015 | Brown et al. |
| 2018/0291364 A1* | 10/2018 | Liberti ............... B01D 15/3885 |

FOREIGN PATENT DOCUMENTS

| | | | |
|---|---|---|---|
| CN | 201396935 Y | 2/2010 | |
| DE | 20 2009 006 839 U1 | 8/2009 | |
| DE | 10 2008 027 638 A1 | 12/2009 | |
| EP | 0 073 079 B1 | 3/1986 | |
| EP | 0 400 829 A1 | 12/1990 | |
| EP | 0 471 947 A1 | 6/1991 | |
| EP | 1 837 640 A2 | 9/2007 | |
| EP | 1 950 281 A1 | 7/2008 | |
| EP | 2 065 085 A1 | 6/2009 | |
| EP | 2 123 745 A2 | 11/2009 | |
| EP | 2886645 A1 * | 6/2015 | ......... C07K 16/2818 |
| GB | 2491623 A | 12/2012 | |
| JP | 58-47485 A | 3/1983 | |
| JP | 61-149080 A | 7/1986 | |
| JP | 3-196836 | 8/1991 | |
| JP | H04-118015 | 4/1992 | |
| JP | H04-122618 | 11/1992 | |
| JP | 05-168463 A | 7/1993 | |
| JP | 08-70845 A | 3/1996 | |
| JP | 8-501927 | 3/1996 | |
| JP | 9-14837 | 1/1997 | |
| JP | H10-505542 | 6/1998 | |
| JP | H10-216446 | 8/1998 | |
| JP | 11-512968 A | 11/1999 | |
| JP | H11-333239 | 12/1999 | |
| JP | 2002-3505 | 1/2002 | |
| JP | 2004-271031 | 9/2004 | |
| JP | 2007-534335 | 11/2007 | |
| JP | 2009-50838 | 3/2009 | |
| JP | 2009-539408 | 11/2009 | |
| JP | 2009-291192 | 12/2009 | |
| JP | 2012-170364 A | 9/2012 | |
| KR | 101152862 | 6/2012 | |
| WO | 94/01530 | 1/1994 | |
| WO | 2003/092849 A1 | 11/2003 | |
| WO | 2006/116139 | 11/2006 | |
| WO | 2009/093995 A1 | 7/2009 | |
| WO | 2009/146769 A | 12/2009 | |
| WO | 2011/041508 A1 | 4/2011 | |
| WO | 2011/078773 A1 | 6/2011 | |
| WO | 2011/110726 A1 | 9/2011 | |
| WO | 2012/170878 A2 | 12/2012 | |
| WO | 2013/009668 A2 | 1/2013 | |
| WO | 2013/032392 A1 | 3/2013 | |
| WO | 2013/053779 A1 | 4/2013 | |
| WO | 2016/164635 A1 | 10/2016 | |

OTHER PUBLICATIONS

G. Catapano et al., *Bioreactor Design and Scale Up*, Chapter 5 of Cell and Tissue Reaction Engineering, 2009, pp. 173-259.

Minghui Hu et al., *Study of an Efficient Temperature Measurement for an Industrial Bioreactor*, ScienceDirect, Measure, vol. 44, 2011, pp. 875-880.

Zhiwei Zhou et al., *Optimizing of Bioreactor Heat Supply and Material Feeding by Numberical Calculation*, ICICIS, 2011, pp. 195-202.

Discovery Scientific Product Lines, Discovery Scientific, http://discoveryscientific.com/products-by-type2/b/mammalian-insect-cell-culture-bioreactor, Apr. 25, 2014, 3 pages.

DASbox Single-Use Vessel, Brochure, DASGIP Information and Process Technology, GMBH, 2012, 2 pages.

* cited by examiner

FLEXIBLE BIOPROCESSING CONTAINER WITH PARTIAL DIVIDING PARTITION

BACKGROUND

1. Technical Field

The present disclosure relates to systems, methods, and products for separating magnetic particles from a fluid.

2. Related Technology

Activation and expansion of human T cells may include introducing feeder cells (e.g., antigen-presenting cells) or T-cell activating antibodies to T-cell culture. Post-activation and expansion removal of the antibodies or antigen-presenting feeder cells, however, may require laborious purification. Alternatively, more sophisticated magnetic bead systems may introduce into the cell culture an amount of magnetic beads that are covalently coupled to specific antibodies (e.g., anti-CD3, anti-CD28, anti-CD137, etc.), which may provide primary and co-stimulatory signals, optimized for efficient T cell activation and expansion. The magnetic beads may then be removed using a magnetic device. For instance, the magnetic bead-containing culture may be exposed to (e.g., fluidly passed over) a magnetic device that retains the antibody-bound magnetic beads, allowing the activated and expanded T-cells to be purified away from the beads.

By way of illustration, FIG. 1 of the present disclosure depicts a magnetic bead-removal bag 10 having an internal compartment 12, an inlet 14, and an outlet 16 (or vice versa). Bag 10 can be placed on a magnetic device (such as a DYNAMAG CTS™ magnet) so that as the magnetic bead-containing culture is introduced into compartment 12 through inlet 14, a magnetic field 18 generated inside compartment 12 by the magnetic device retains at least some of the magnetic beads that are exposed to magnetic field 18. A product is then recovered through outlet 14.

One problem with existing systems is that some of the magnetic beads may not retained by magnetic field 18 and, therefore, contaminate the product recovered through outlet 16. To remove substantially all of the magnetic beads, the mixture may need to be exposed to magnetic field 18 multiple times. For instance, the mixture may need to be circulated through bag 10 multiple times (e.g., twice, or more than twice) in order to re-expose the magnetic beads to magnetic field 18. Alternatively, or in addition, users may ensure that the magnetic bead-containing culture flows through compartment 12 at a low flow rate to ensure that the magnetic beads are exposed to magnetic field 18 for a sufficient amount of time (e.g., less than 20-30 mL/min). Other solutions include wrapping an outlet tube that extends from outlet 16 around a secondary magnet so that the recovered product is exposed to a second magnetic field that retains the magnetic beads within the outlet tubing. Recirculation, reduced flow rate, and secondary magnets can increase the time and cost required for removing the magnetic beads from the mixture. Time-consuming measures add expensive delay and require operator monitoring in commercial applications. Costly additional components (e.g., magnets) also increase the overall cost of sample production and purification.

Accordingly, there are a number of disadvantages with conventional magnetic bead-removal systems that can be addressed.

BRIEF SUMMARY

Embodiments of the present disclosure solve one or more of the foregoing or other problems in the art with systems, methods, and products for separating magnetic particles from a fluid. Methods can include introducing a fluid mixture into an internal compartment of a container. The container can be flexible. For instance, the container can be or comprise a flexible bag. The fluid mixture can be introduced into the internal compartment through an inlet of the container. The inlet can be in fluid communication with the internal compartment. The fluid mixture can include a liquid media. The fluid mixture can include a biological component. The fluid mixture can include magnetic particles.

Some embodiments include allowing at least a portion of the mixture to travel around a partition. The partition can be formed within the internal compartment. Some embodiments include allowing at least a portion of the mixture to exit the internal compartment through an outlet. The outlet can be disposed on the opposite side of the partition from the inlet. The outlet can be in fluid communication with the internal compartment.

Some embodiments include applying a magnetic field. The magnetic field can be applied to the mixture. The magnetic field can be applied in the internal compartment. The magnetic particles are, can be, or become retained within the container or internal compartment thereof by or by means of the magnetic field. In some embodiments, the magnetic particles are, can be, or become retained within the container or internal compartment thereof by or by means of the magnetic field as the media and biological component flow from the inlet, around the partition and to the outlet.

In some embodiments, the biological component comprises cells. In some embodiments, the cells comprise activated and/or expanded human T-cells. In some embodiments, the biological component comprises one or more nucleic acids, proteins, such as antibodies, fats, fatty acids, or combination(s), aggregate(s), or precipitate(s) thereof.

In some embodiments, the magnetic particles comprise beads. In some embodiments, the magnetic particles comprise inert, superparamagnetic beads. In some embodiments, the beads have one or more anti-CD3 antibodies coupled thereto. In some embodiments, the beads have one or more anti-CD28 antibodies coupled thereto. In some embodiments, the beads have one or more anti-CD3 and one or more anti-CD28 antibodies coupled thereto. The beads can optionally have a substantially uniform diameter. The diameter can be about 4.5 µm.

In some embodiments, the fluid mixture comprises a suspension cell culture. The suspension cell culture can comprise cells. The cells can be growing in a liquid media. In some embodiments, the suspension cell culture is disposed in a bioreactor. In some embodiments, the introduced fluid mixture optionally flows from the bioreactor into the internal compartment of the container. In some embodiments, the fluid mixture is introduced into the internal compartment at a flow rate greater than or equal to about 20-30 mL/min. In some embodiments, the portion of the fluid mixture that exits the internal compartment through the outlet comprises less than 5000, preferably less than 1000, more preferably less than 100, most preferably less than 20 magnetic particles per milliliter of liquid media.

Some embodiments may include any of the features, options, and/or possibilities set out elsewhere in the present disclosure, including in other aspects or embodiments of the present disclosure.

Some embodiments include disposing the container on or in a magnetic field-generating device. Some embodiments include closing a lid of the magnetic field-generating device. The lid can be closed against the container such that at least a portion of the container becomes flattened into a substantially two-dimensional configuration.

In some embodiments, the flexible container comprises an upper container wall. In some embodiments, the flexible container comprises a lower container wall. The upper and lower container walls can be joined at an encircling perimeter. In some embodiments, the partition can comprise a joinder of the upper container wall and lower container wall. In some embodiments, the partition can extend from the perimeter into the internal compartment.

In some embodiments, the inlet extends through the joined perimeter. In some embodiments, the outlet extends through the joined perimeter. In some embodiments, the partition comprises at least one weld between the upper container wall and lower container wall. Some embodiments include forming the partition by reversibly pressing together the upper container wall and the lower container wall. Some embodiments include forming the partition by reversibly pressing together the upper container wall and the lower container wall such that the media and biological component flow or must flow around the partition. Some embodiments include forming the partition by reversibly pressing together the upper container wall and the lower container wall such that the media and biological component flow or must flow around the partition to flow through the outlet.

In some embodiments, the partition extends from a first location. The first location can be disposed proximal to the inlet. The first location can be disposed proximal to the outlet. In some embodiments, the first location is disposed between the inlet and the outlet. In some embodiments, the first location is disposed between and proximal to the inlet and the outlet. In some embodiments, the partition extends to a second location. The second location can be disposed within the internal compartment. The second location can be disposed distal to the inlet. The second location can be disposed distal to the outlet. In some embodiments, the partition extends from a first location to a second location.

In some embodiments, the inlet comprises a first opening. The first opening can have a first diameter. In some embodiments, the outlet comprising a second opening. The second opening can have a second diameter. In some embodiments, the first opening is in fluid communication with the internal compartment. In some embodiments, the second opening is in fluid communication with the internal compartment.

In some embodiments, the partition extends beyond at least the first opening. In some embodiments, the partition extends beyond at least the first opening a first distance. In some embodiments, the partition extends beyond at least the first opening a first distance into the internal compartment. In some embodiments, the first distance can be at least half the first diameter. In some embodiments, the first distance can be less than 10 times, 50 times, 100 times, 150 times, 200 times, 250 times, 300 times or 350 times the first diameter. In some embodiments, the partition extends beyond the second opening.

In some embodiments, the partition extends beyond the second opening. In some embodiments, the partition extends beyond the second opening the first distance. In some embodiments, the partition extends beyond the second opening a second distance. In some embodiments, the partition extends beyond the second opening the first distance into the internal compartment. In some embodiments, the partition extends beyond the second opening a second distance into the internal compartment. In some embodiments, the second distance is less than the first distance. In some embodiments, the second distance is greater than the first distance. In some embodiments, the first distance is equal to the first distance.

In some embodiments, the first opening is disposed on, at, or in a first side of the container. In some embodiments, second opening is disposed on, at, or in the first side of the container. In some embodiments, second opening is disposed on, at, or in a second side of the container. The second side of the container can be disposed opposite the first side of the container. In some embodiments, the first and second openings are disposed on, at, or in opposite first and second sides of the partition.

In some embodiments, the first opening comprises a tubular member. In some embodiments, the second opening comprises a tubular member. In some embodiments, the tubular member(s) can extend through the joined perimeter. In some embodiments, the tubular member(s) can extend through the flexible container. In some embodiments, the tubular member(s) can extend through the upper container wall. In some embodiments, the tubular member(s) can extend through the lower container wall.

In some embodiments, at least a portion of the container is disposed on or in a magnetic field-generating device. The device can produce a magnetic field within at least a portion of the compartment. The device can be producing a magnetic field within at least a portion of the compartment.

Some embodiments include introducing a first fluid mixture into a flexible container. Some embodiments include introducing a first fluid mixture into an internal compartment of a flexible container. Some embodiments include introducing a first fluid mixture into an internal compartment of a flexible container through a first opening.

In some embodiments, the first mixture comprises a liquid media. In some embodiments, the first mixture comprises a first amount of magnetic particles. The first amount of magnetic particles can be disposed in the liquid media. The biological component can be disposed in the liquid media. The biological component can be disposed in the liquid media at a first concentration.

Some embodiments can include removing a second fluid mixture from the compartment. The second fluid mixture can be removed from the compartment through a second opening. The second opening can be disposed in the first side of the container. The second opening can be disposed adjacent to the first opening. The second mixture can comprise the liquid media. The second mixture can comprise the liquid media the biological component. The biological component can be disposed in the liquid media. The biological component can be disposed in the liquid media at a second concentration. The second concentration can be greater than the first concentration. The second concentration can be greater than 80%, 85%, 90%, 95%, 96%, 97%, 98%, or 99% of the first concentration. The second fluid can have or comprise less than 5000 magnetic particles per milliliter of liquid media, preferably less than 1000 magnetic particles per milliliter of liquid media, more preferably less than 100 magnetic particles per milliliter of liquid media, even more preferably less than 20 magnetic particles per milliliter of liquid media.

The magnetic field can retain at least a portion of the first amount of magnetic particles in the compartment. The compartment can have a partition formed therein. The partition can be or comprise a joinder of the upper container wall and lower container wall. The partition can have a sealed first end extending from the first side of the container. The partition can have a sealed first end extending from the first side of the container adjacent to the first opening. The partition can have a sealed first end extending from the first side of the container between the first opening and the second opening. The partition can have a second end opposite the first end. The second end can be disposed at a second location within the compartment. In some embodiments, the liquid media and the biological component must pass from the first opening, around the partition, and to the second opening in order to be removed from the compartment.

Some embodiments may include any of the features, options, and/or possibilities set out elsewhere in the present disclosure, including in other aspects or embodiments of the present disclosure.

Some embodiments can include a magnetic particle separation system, comprising (i) a magnetic field generating device, the magnetic field generating device comprising a (a) receiving area having an upper surface, and (b) a magnetic field generating element disposed beneath the upper surface of the receiving area, the magnetic field generating element configured to produce a magnetic field above the surface, and (ii) a container assembly disposed on the surface, the container assembly comprising (a) a flexible container comprising an outer wall having an interior surface that at least partially bounds an internal compartment, (b) a fluid inlet extending through the outer wall, the inlet being in fluid communication with the compartment, (c) a fluid outlet extending through the outer wall, the outlet being adjacent to the inlet, the outlet being in fluid communication with the compartment, and (d) a first partition formed in the internal compartment, the partition comprising a joinder of opposing sides of the interior surface between the fluid inlet and the fluid outlet.

In some embodiments, the magnetic field generating device further comprises a lid. The lid can be disposed over the upper surface of the receiving area. At least a portion of the flexible container can be disposed between the upper surface and the lid. At least a portion of the flexible container can be disposed between the upper surface and the lid such that such that at least a portion of the flexible container becomes flattened into a substantially two-dimensional configuration. In some embodiments, the outer wall of the flexible container comprises an upper container wall and a lower container wall joined at an encircling perimeter. The outer wall can be formed of a flexible, polymeric, water impermeable sheet material.

In some embodiments, the fluid inlet comprises a first opening disposed in the outer wall or extending through the joined perimeter on a first side of the container, the first opening being in fluid communication with the internal compartment. In some embodiments, the fluid outlet comprises a second opening disposed in the outer wall or extending through the joined perimeter on the first side of the container adjacent to the first opening, the second opening being in fluid communication with the internal compartment. In some embodiments, the first partition extends from the perimeter into the internal compartment. The first partition can comprise a joinder of the upper container wall and the lower container wall, the first partition having a sealed first end extending from the first side of the container between the first opening and the second opening and a second end opposite the first end disposed at a second location within the internal compartment such that a fluid passing from the fluid inlet to the fluid outlet must flow around the second end of the first partition as direct, linear access between the fluid inlet and the fluid outlet is restricted by the first partition. In some embodiments, the first opening has a first diameter and the second opening has a second diameter, the partition extending beyond at least the first opening a first distance into the internal compartment, the first distance being at least half the first diameter and less than 10 times, 50 times, 100 times, 150 times, 200 times, 250 times, 300 times or 350 times the first diameter.

In some embodiments, the magnetic field generating device further comprises a fluid mixture disposed in the internal compartment, the fluid mixture comprising a liquid media, a biological component, and magnetic particles. In some embodiments, the magnetic field generating device further comprises a magnetic field produced by the magnetic field generating element above the upper surface and within the internal compartment, the magnetic particles being secured to the interior surface by the magnetic field. In some embodiments, the biological component comprises activated human T-cells. In some embodiments, the magnetic particles comprise beads. In some embodiments, the magnetic particles comprise inert, superparamagnetic beads. In some embodiments, the beads have one or more anti-CD3 antibodies coupled thereto. In some embodiments, the beads have one or more anti-CD28 antibodies coupled thereto. In some embodiments, the beads have one or more anti-CD3 and one or more anti-CD28 antibodies coupled thereto. The beads can optionally have a substantially uniform diameter. The diameter can be about 4.5 µm. The fluid mixture can comprise a suspension cell culture of the human T-cells in the liquid media. The fluid mixture can comprise a suspension cell culture of the human T-cells growing in the liquid media. In some embodiments, the system further comprises a bioreactor fluidly coupled to the internal compartment of the container.

Some embodiments may include any of the features, options, and/or possibilities set out elsewhere in the present disclosure, including in other aspects or embodiments of the present disclosure.

Some embodiments include a container assembly, comprising (i) a flexible container comprising an outer wall having an interior surface that at least partially bounds an internal compartment, the outer wall comprising an upper container wall and a lower container wall joined at an encircling perimeter, the outer wall being formed of a flexible, polymeric, water impermeable sheet material, (ii) a fluid inlet comprising a first opening disposed in the outer wall or extending through the joined perimeter on a first side of the container, the first opening being in fluid communication with the internal compartment, the first opening having a first diameter, (iii) a fluid outlet comprising a second opening disposed in the outer wall or extending through the joined perimeter on the first side of the container adjacent to the first opening, the second opening being in fluid communication with the internal compartment, the second opening having a second diameter, and (iv) a first partition formed in the internal compartment and extending from the perimeter into the internal compartment a first distance beyond at least the first opening, the first distance being at least half the first diameter and less than 350 times the first diameter, the first partition comprising a joinder of the upper container wall and the lower container wall, the first partition having a sealed first end extending from the first side of the container between the first opening and the second opening and a second end opposite the first end disposed within the internal compartment such that a fluid passing from the fluid inlet to the fluid outlet must flow around the first partition, and such that direct, linear access between the fluid inlet and the fluid outlet is restricted by the first partition.

Some embodiments may include any of the features, options, and/or possibilities set out elsewhere in the present disclosure, including in other aspects or embodiments of the present disclosure. It is also noted that each of the foregoing, following, and/or other features described herein represent a distinct embodiment of the present disclosure. Moreover, combinations of any two or more of such features represent distinct embodiments of the present disclosure. Such features or embodiments can also be combined in any suitable combination and/or order without departing from the scope of this disclosure. Thus, each of the features described herein can be combinable with any one or more other features described herein in any suitable combination and/or order. Accordingly, the present disclosure is not limited to the specific combinations of exemplary embodiments described in detail herein.

Additional features and advantages of exemplary embodiments of the present disclosure will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which certain advantages and features of the present disclosure can be obtained, a description of the disclosure will be rendered by reference to specific embodiments thereof which are illustrated in the appended drawings. Understanding that these drawings depict only typical embodiments of the disclosure and are not therefore to be considered to be limiting of its scope, the disclosure will be described and explained with additional specificity and detail through the use of the accompanying drawings in which.

DETAILED DESCRIPTION

Figure 1:
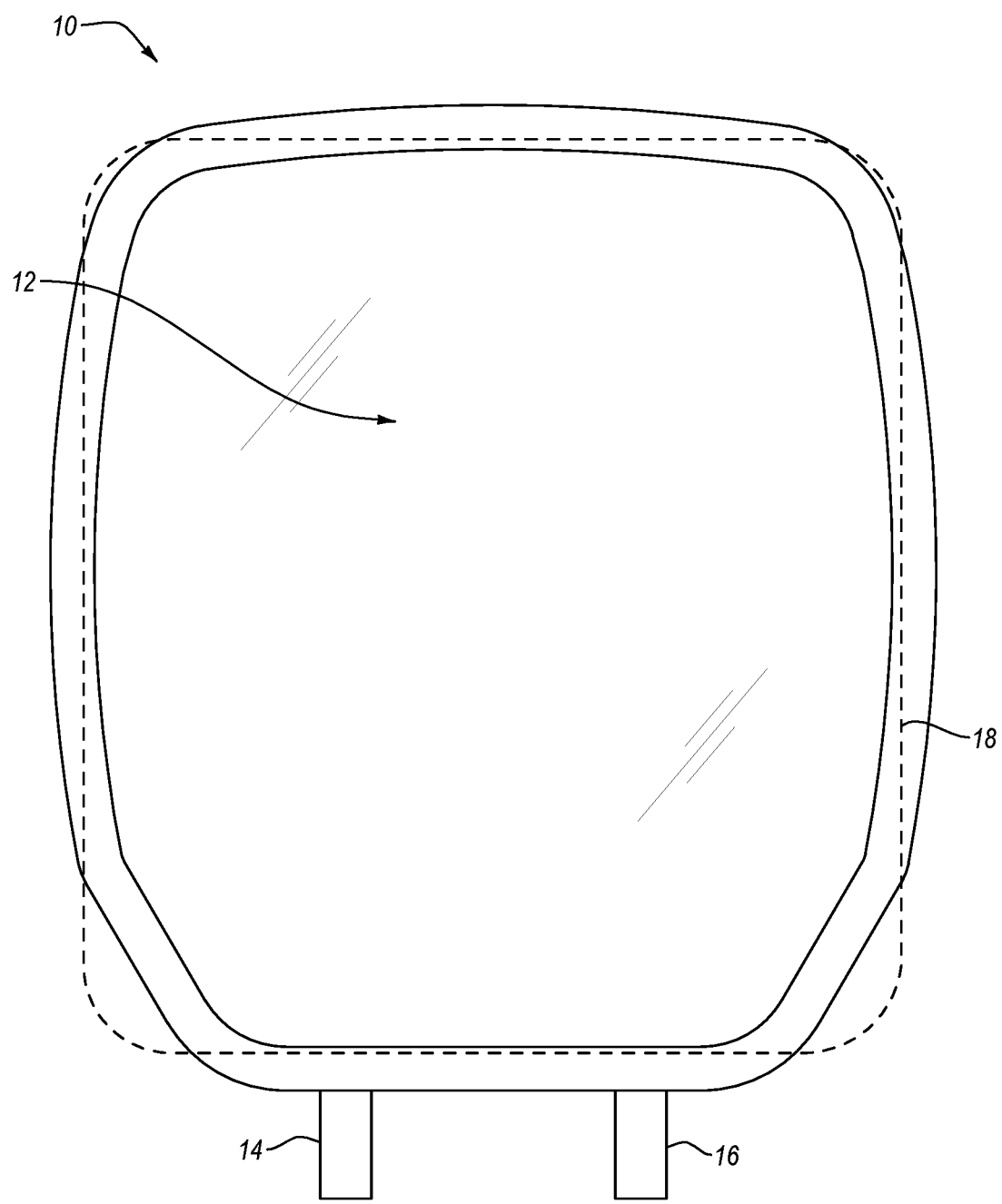
FIG. 1 is a top plan view of an existing bag.

Before describing various embodiments of the present disclosure in detail, it is to be understood that this disclosure is not limited to the specific parameters and description of the particularly exemplified systems, methods, and/or products that may vary from one embodiment to the next. Thus, while certain embodiments of the present disclosure will be described in detail, with reference to specific features (e.g., configurations, parameters, properties, steps, components, ingredients, members, elements, parts, and/or portions, etc.), the descriptions are illustrative and are not to be construed as limiting the scope of the present disclosure and/or the claimed invention. In addition, the terminology used herein is for the purpose of describing the embodiments, and is not necessarily intended to limit the scope of the present disclosure and/or the claimed invention.

Unless defined otherwise, all technical and scientific terms used herein have the same meaning as commonly understood by one of ordinary skill in the art to which the present disclosure pertains.

Various aspects of the present disclosure, including systems, processes, and/or products may be illustrated with reference to one or more embodiments or implementations, which are exemplary in nature. As used herein, the terms "embodiment" and implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "partition" includes one, two, or more partitions.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible. Specific language will be used herein to describe the exemplary embodiments. Nevertheless it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. Furthermore, an element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein.

The headings used herein are for organizational purposes only and are not meant to be used to limit the scope of the description or the claims.

The present invention relates to systems, methods, and products for separating magnetic particles from a fluid. Methods can include introducing a fluid mixture into an internal compartment of a container through an inlet. The fluid mixture can include a liquid media, a biological component, and magnetic particles. Methods also include allowing at least a portion of the mixture to travel around a partition formed within the internal compartment. The mixture can then exit the internal compartment through an outlet (e.g., on the opposite side of the partition from the inlet). Methods also include applying a magnetic field to the mixture (e.g., in the internal compartment) so that the magnetic particles are retained within the container or internal compartment thereof by the magnetic field.

As used herein, the term "systems" also contemplates devices, apparatus, compositions, assemblies, kits, and so forth. Similarly, the term "products" also contemplates devices, apparatus, compositions, assemblies, kits, and so forth. Moreover, the term "methods" also contemplates processes, procedures, steps, and so forth.

As used herein, the term "fluid mixture" can comprise any suitable composition and/or combination of the specific components thereof. For instance, the mixture can comprise a solution, suspension, colloid, emulsion, or other mixture (e.g., in which the biological component and magnetic particles are disposed in the fluid (e.g., liquid) media.

As used herein, the term "biological component" includes one or more cells (e.g., T-cells, whether human or non-human, activated or inactivated, etc.), molecules (e.g., elements), compounds (e.g., nucleic acids, proteins, such as antibodies, fats, fatty acids, etc.), or combination(s), aggregate(s), or precipitate(s) thereof.

As used herein, the term "magnetic particle," and the like, refers to a component that responds (magnetically) to and/or is (magnetically) susceptible to a magnetic field. The component can comprise or be formed of material that is attracted into and/or repelled out of a magnetic field. In some embodiments, the component can comprise a paramagnetic or superparamagnetic particle (or magnetic bead). The bead can comprise a (substantially spherical) polymer (e.g., polystyrene). The polymeric bead can have a uniform size and a consistent, defined surface (e.g., useful for the adsorption or coupling of one or more bioreactive molecules or cells). In at least some embodiments, the bead can have a diameter greater than 50 nm (e.g., the approximate size of magnetic-activated cell sorting beads). In certain embodiments, the bead can be between 1 nm and 100 mm, between 100 nm and 1 mm, between 500 nm and 100 μm, between 1 μm and 10 μm, between 1 μm and 5 μm, or between 4 μm and 5 μm in diameter. In certain embodiments, the bead can be (covalently) linked to a molecule and/or compound (e.g., an antibody that recognizes a specific protein on the surface of the target cell-type).

As used herein, the term "diameter," whether in reference to the size of a particle (e.g., a bead) or other component (e.g., an opening), is not limited to the measurement of circular or spherical components. Rather, whether circular, oval or oblong, rectangular, angle or jagged, or a combination thereof, the diameter of the component can refer to a (cross-sectional) measurement between opposing sides and/or the (maximum or minimum) distance between the opposing sides.

Reference will now be made the figures of the present disclosure. It is noted that the figures are not necessarily drawn to scale and that the size, orientation, position, and/or relationship of or between various components can be altered in some embodiments without departing from the scope of this disclosure.

Figure 2A:
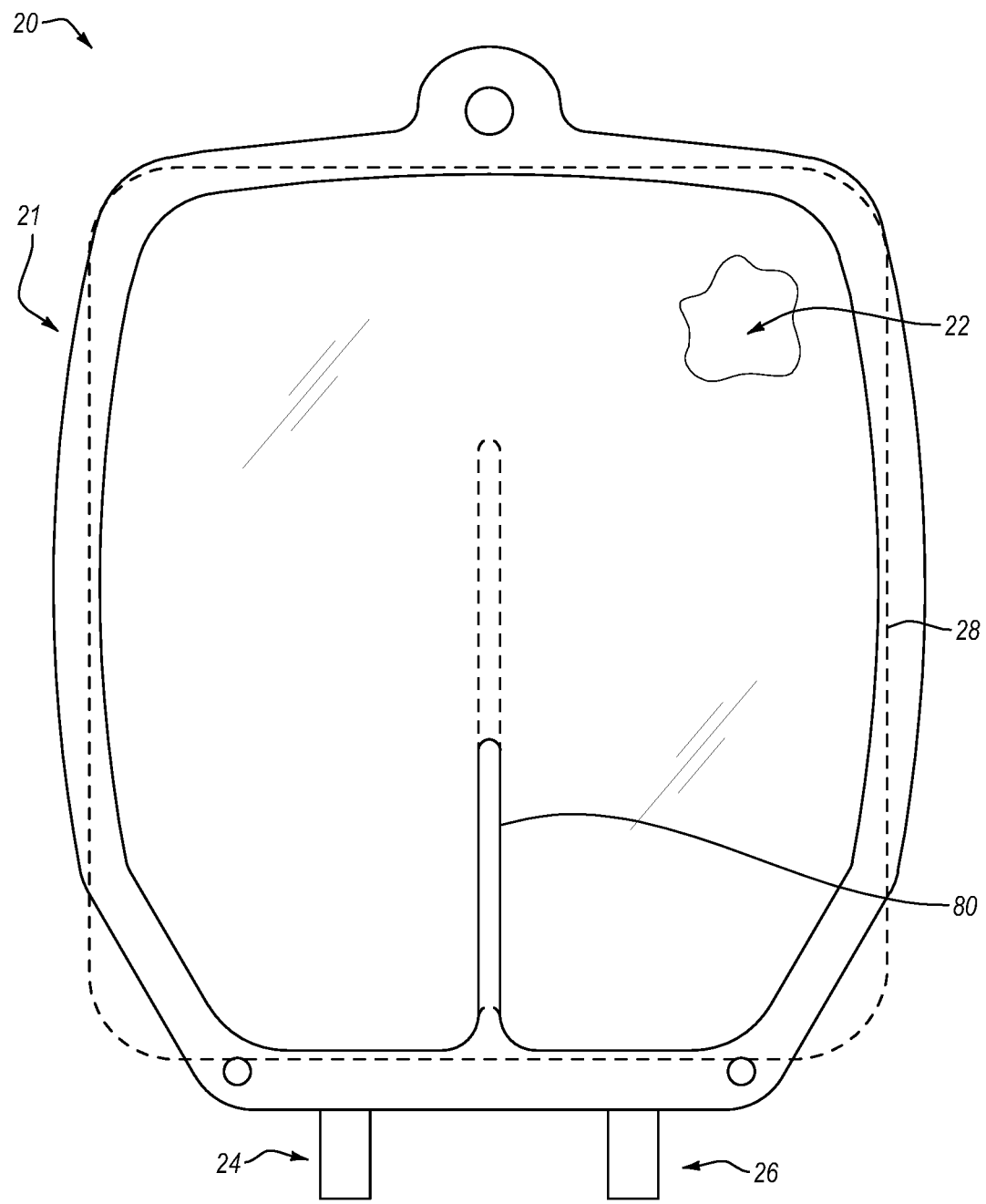
FIG. 2A is a top plan view of a container assembly according to an embodiment of the present disclosure.
Figure 2B:
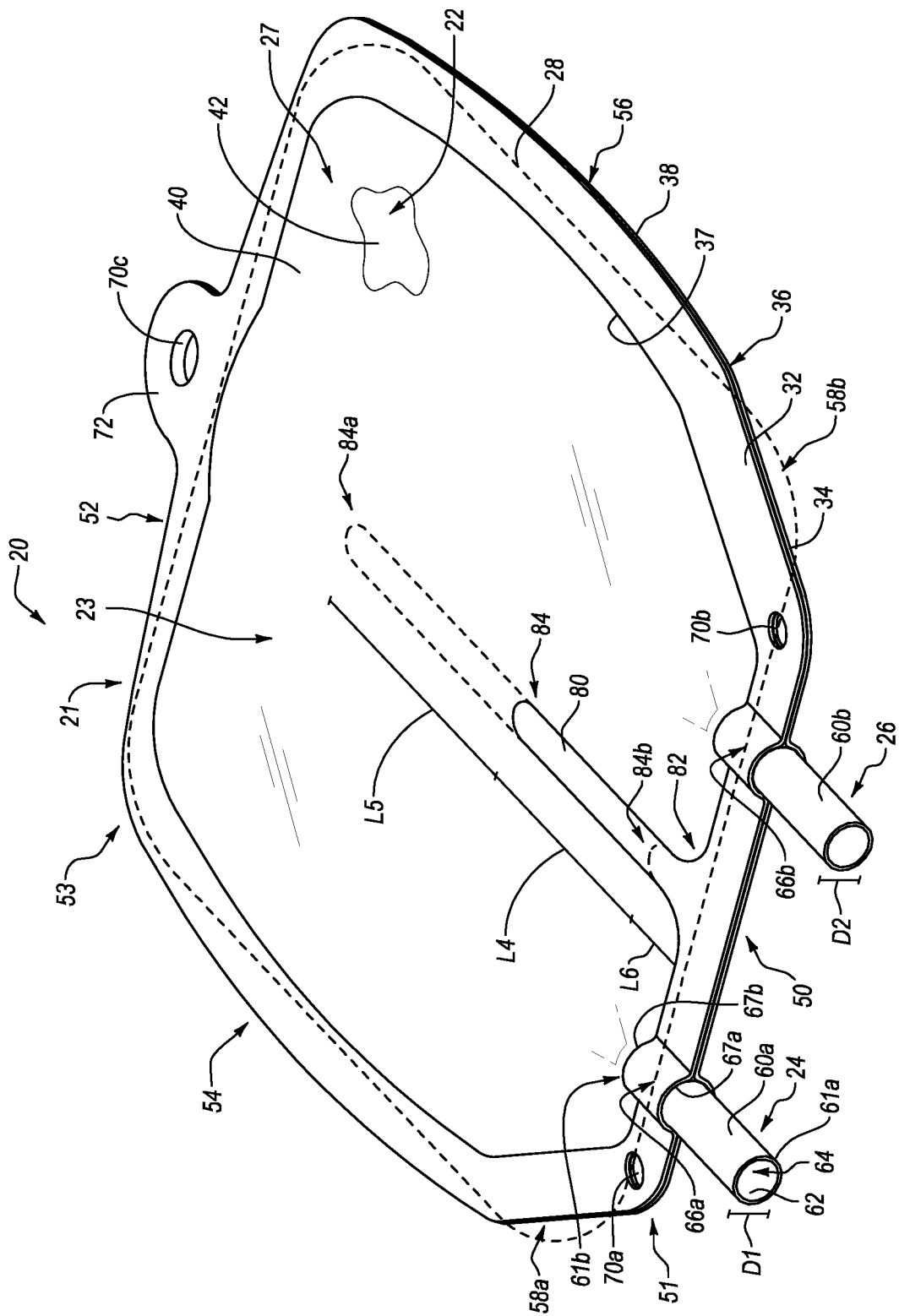
FIG. 2B is a perspective view of the container assembly of FIG. 2A.

Depicted in FIG. 2A and FIG. 2B is one embodiment of a container assembly 20 incorporating features of the present disclosure. In general, container assembly 20 comprises a container 21, an inlet 24, and outlet 26, and a partition 80.

Containers

In the depicted embodiment, container 21 comprises a flexible (e.g., pliable, malleable, bendable, etc.) and/or collapsible, pillow type bag that is formed from two overlapping sheets of polymeric material (i.e., film) that are seamed together around a perimeter 36. In particular, container 21 comprises an upper container wall (or sheet) 32 and a lower container wall (or sheet) 34 disposed in an overlapping relationship, with sheets 32 and 34 joined together at their peripheries to form an (encircling) perimeter 36 to form an outer wall 27 of container 21. Outer wall 27 (or each sheet 32 and 34 thereof) has an exterior surface 40 and an opposing interior surface that bounds an internal compartment 22. Perimeter 36 forms a water impermeable seal at the interface between sheets 32 and 34. For instance, perimeter 36 can comprise a weld between sheets 32 and 34.

Perimeter 36 (or the weld thereof) has an inner perimeter edge 37 facing compartment 22 and an outer perimeter edge 38 extending around the exterior of container 21. Perimeter 36 also comprises a first or lower perimeter edge 50 disposed on a first side (or lower end) 51 of container 21 and an opposing second or upper perimeter edge 52 disposed on a second side (or upper end) 53 of container 21. Container 21 also has opposing side perimeter edges 54 and 56 extending between first perimeter edge 50 and opposing second perimeter edge 52. In the depicted embodiment, container 21 further includes opposing transition perimeter edges 58a and 58b disposed at the transition between first perimeter edge 50 and opposing side perimeter edges 54 and 56, respectively. Accordingly, edges 50, 52, 54, 56, 58a, and 58b combine to form perimeter (edge) 36.

Transition perimeter edges 58a, 58b are angled relative to first perimeter edge 50 and opposing side perimeter edges 54 and 56, respectively. In particular, first perimeter edge 50 and opposing side perimeter edges 54 and 56, respectively, can be disposed and/or oriented substantially perpendicular (i.e., 90 degree angle relative) to one another. Transition perimeter edges 58a, 58b can be disposed and/or oriented at an approximately 45 degree angle relative to first perimeter edge 50 and opposing side perimeter edges 54 and 56, respectively. It will be appreciated, however, that a variety of configurations, including rounded, multi-angular, and so forth, can also be suitable for transition perimeter edges 58a, 58b. Regardless of specific configuration, transition perimeter edges 58a, 58b can occupy, remove, and/or eliminate a portion (e.g., a lower corner portion between first perimeter edge 50 and opposing side perimeter edges 54 and 56, respectively) of compartment 22, thereby reducing the volume or area of internal compartment 22 and/or the lower corner portion. Certain alternative embodiments need not include one or more of transition perimeter edges 58a, 58b.

A plurality of openings 70 transversely extend through perimeter 36. For instance, opposing first opening 70a and second opening 70b are disposed at the corner or interface between first perimeter edge 50 and transition edges 58a, 58b, respectively. Container 21 also has a securing tab 72 disposed at and/or extending from upper perimeter edge 52. A third opening 70c extends through securing tab 72. While openings 70 extend through perimeter 36 of container 21 or outer wall 27 thereof, openings 70 do not communicate with compartment 22. Rather, openings 70 extend through the welded perimeter edge portion of container 21 between inner perimeter edge 37 and outer perimeter edge 38 thereof.

Figure 3:
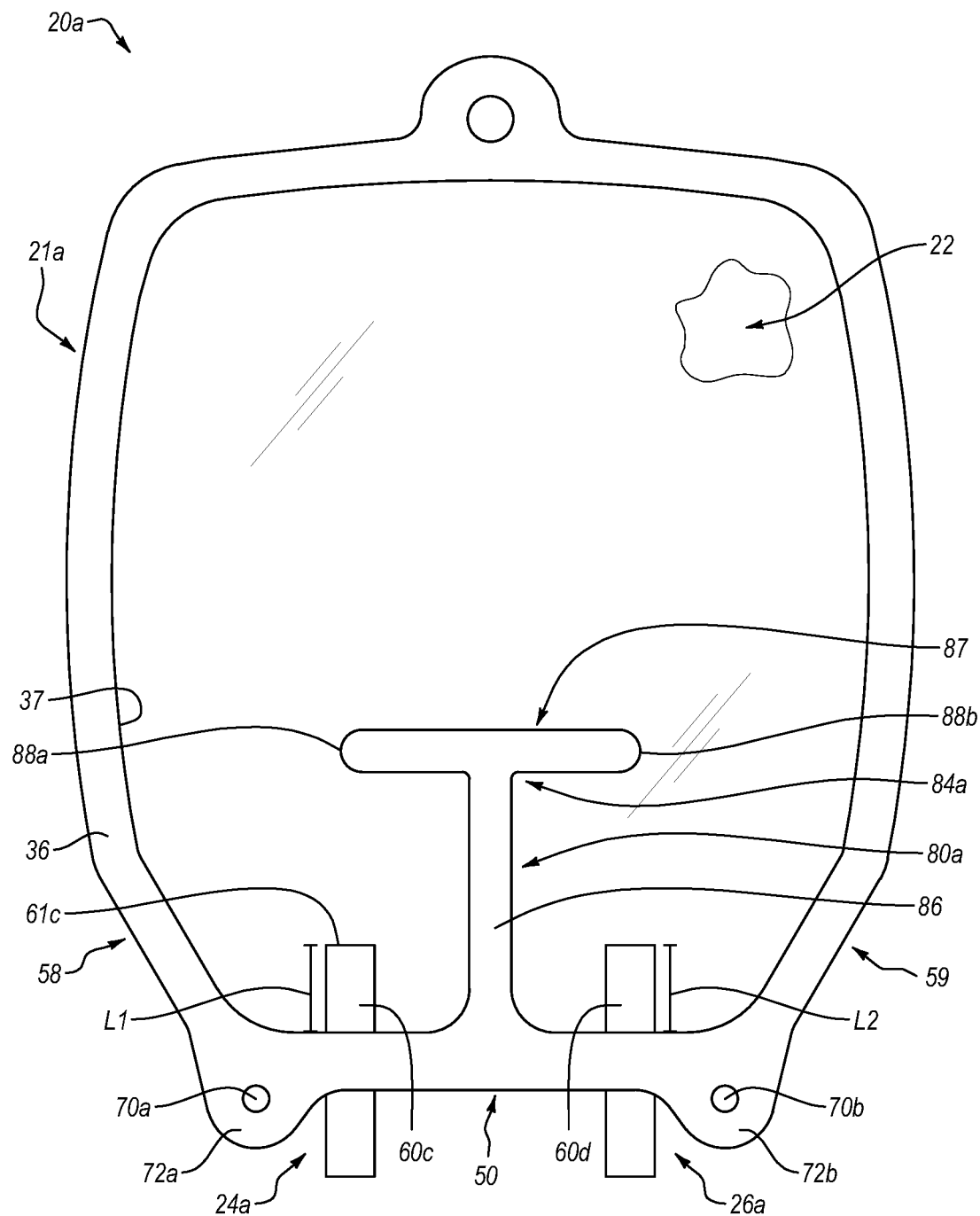
FIG. 3 is a top plan view of a container assembly according to another embodiment of the present disclosure.

FIG. 3 depicts an alternative container assembly 20a comprising a container 21a. Container 21a can be similar to container 21 in most respects. Unlike container 21, however, container 21a (or perimeter 36 thereof) includes opposing securing tabs 72. Specifically, a first securing tab 72a extends from first perimeter edge 50, first transition perimeter edge 58a, or the corner therebetween. Similarly, a second securing tab 72b extends from first perimeter edge 50, second transition edge 58b, or the corner therebetween.

Regardless of specific configuration, shape, size, etc., container 21, 21a of the present disclosure can be comprised of any material suitable for the forming such bags. In at least one embodiment, container 21, 21a can be comprised of water impermeable material such as a low-density polyethylene or other polymeric film having a thickness in a range between about 0.1 mm to about 5 mm with about 0.2 mm to about 2 mm being more common. The polymeric film can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. The film is typically sufficiently flexible that it can be rolled into a tube without plastic deformation and/or can be folded over an angle of at least 90°, 180°, 270°, or 360° without plastic deformation.

The material can be comprised of a single ply film or can comprise two or more layers which are either sealed together or separated to form a double wall container. Where the layers are sealed together, the film can comprise a laminated or extruded material. The laminated material comprises two or more separately formed layers that are subsequently secured together by an adhesive. The laminated and extruded films typically have between 1-9 layers and more commonly between 3-9 layers. The films used can commonly have a number of layers that is at least or less than 1, 3, 5, 7, or 9 layers or in a range between any two of the foreogiong. The extruded film can be a cast film such as a multi-layer co-extruded cast film.

Some extruded materials comprise a single integral sheet that comprises two or more layers of different materials that can be separated by a contact layer. All of the layers can be simultaneously co-extruded. One example of an extruded material that can be used in the present invention is the Thermo Scientific CX3-9 film available from Thermo Fisher Scientific. The Thermo Scientific CX3-9 film is a three-layer, 9 mil cast film produced in a cGMP facility. The outer layer is a polyester elastomer coextruded with an ultra-low density polyethylene product contact layer. Another example of an extruded material that can be used in the present invention is the Thermo Scientific CX5-14 cast film also available from Thermo Fisher Scientific. The Thermo Scientific CX5-14 cast film comprises a polyester elastomer outer layer, an ultra-low density polyethylene contact layer, and an ethylene vinyl alcohol (EVOH) barrier layer disposed therebetween. In still another example, a multi-web film produced from three independent webs of blown film can be used. The two inner webs are each a 4 mil monolayer polyethylene film while the outer barrier web is a 5.5 mil thick 6-layer co-extrusion film.

In some embodiments, the material can be approved (by a government or regulatory agency or other organization) for direct contact with living cells and/or capable of maintaining a solution sterile. In such an embodiment, the material can also be sterilizable such as by ionizing radiation. Examples of materials that can be used in different situations are disclosed in U.S. Pat. No. 6,083,587 which issued on Jul. 4, 2000 and United States Patent Publication No. US 2003-0077466 A1, published Apr. 24, 2003 which are hereby incorporated by specific reference.

In at least one embodiment, container 21, 21a comprises a two-dimensional, pillow style bag wherein two sheets of material are placed in overlapping relation and the two sheets are bounded together at their peripheries to form an (encircling) perimeter. The bounded sheets also form internal compartment 22 therebetween. Alternatively, a single sheet of material can be folded over and seamed around (at least some (e.g., the free edges) of) the periphery to form internal compartment 22. In another embodiment, the containers can be formed from a continuous tubular extrusion of polymeric material that is cut to length and is seamed closed at the (free or open) ends thereof.

In still other embodiments, container 21, 21a can comprise a three-dimensional bag that not only has an annular side wall but also a two dimensional top end wall and a two dimensional bottom end wall. Three dimensional containers comprise a plurality of discrete panels, typically three or more, and more commonly four or six. Each panel comprises a portion of an encircling side wall, top end wall, and bottom end wall of the container. Corresponding perimeter edges of each panel can be seamed together. The seams are typically formed using methods known in the art such as heat energies, radiofrequency (RF) energies, sonic energies or sonics, or other sealing energies. In alternative embodiments, the panels can be formed in a variety of different patterns.

It is appreciated that container 21, 21a can be manufactured to have virtually any desired size, shape, and configuration. For example, container 21, 21*a* can be formed having internal compartment 22 sized to at least, greater than, less than, between, or about 100 milliliters, 200 milliliters, 300 milliliters, 400 milliliters, 500 milliliters, 750 milliliters, 1 liter, 2 liters, or other desired volumes, including any volume or range of volumes therebetween. Although container 21, 21*a* can be or have any shape, in some embodiments, container 21, 21*a* is specifically configured to be complementary or substantially complementary (in size, shape, etc.) to the receiving area of a Dynamag™ CTS™ magnetic field generating device.

Although in the above discussed embodiment container 21, 21*a* has a flexible, bag configuration, in alternative embodiments it is appreciated that container 21, 21*a* can comprise any form of collapsible container or semi-rigid container. Container 21, 21*a* can also be opaque or non-opaque (transparent or translucent) and/or can have ultraviolet light inhibitors incorporated therein.

Container Inlets and Outlets

Returning now to FIGS. 2A and 2B, container assembly 20 also includes an inlet 24 and an outlet 26 (as indicated above). Inlet 24 and outlet 26 provide access from the exterior of container 21 to internal compartment 22 thereof. For instance, inlet 24 comprises a first opening 66*a* extending through joined perimeter 36 on first perimeter edge 50 thereof (on first side 51 of container 21). Similarly, outlet 26 comprises a second opening 66*b* extending through perimeter 36 on first perimeter edge 50 thereof adjacent first opening 66*a*. In alternative embodiments, openings 66 (66*a*, 66*b*) can be disposed on or extend through other perimeter edge(s) or outer wall 27 other than through perimeter 36. For instance, openings 66 can extend through upper container wall 32 or lower container wall 34. Although two openings 66 are shown, it is appreciated that container assembly 20 can include and/or be formed with any desired number of openings 66.

Openings 66 each have an exterior opening 67*a* disposed on outer perimeter edge 38, an interior opening 67*b* disposed on inner perimeter edge 37, and a passageway extending therebetween. Openings 66 also have a diameter (as discussed below). In at least one embodiment, the diameters of openings 66*a* and 66*b* can be or have similar measurements. For instance, the diameters can be substantially the same. Alternatively, one diameter can be greater than the other diameter. The diameter of openings 66 can have any suitable measurement. In certain embodiments, however, one or more of the diameters are sized to induce and/or ensure a specific flow rate of fluid therethrough (e.g., in response to a specific pump pressure or speed). For instance, in specific embodiments the diameters can be at least, up to, greater than, less than, between, or about 1 mm, 2 mm, 2.5 mm, 3 mm, 4 mm, 5 mm, 7.5 mm, 10 mm, 15 mm, 20 mm, and so forth, including any diameter or range of diameters therebetween.

In the depicted embodiment, inlet 24 and outlet 26 each comprise a tubular member 60 connected to opening 66. In particular, a first tubular member 60*a* extends at least partially through (or into) first opening 66*a* and a second tubular member 60*b* extends at least partially through (or into) second opening 66*b*. Tubular member 60 can be welded or otherwise connected to container 21 (e.g., seemed into opening 66) during the manufacturing of container 21). Alternatively, tubular member 60 can be coupled with opening 66 (such as by welding) after the manufacturing of container 21. Regardless of specific configuration, tubular member 60 can be connected to opening 66 so as to form a fluid (e.g., liquid) tight seal. Thus, tubular member(s) 60 can also be sterilizable (e.g., simultaneously with container 21) such as by ionizing radiation.

Although two tubular members 60 are shown, it is appreciated that container assembly 20 can include and/or be formed with any desired number of tubular members 60. For instance, in alternative embodiments, one or three or more tubular members 60 can be used. In at least one embodiment, a single, divided tubular member can be connected to an opening 66. The divided tubular member can have two passageways separated by a barrier. The two passageways can function as separate tubular members in certain embodiments.

Tubular member(s) 60 can also be connected at any desired location on container 21. As depicted, tubular members 60 extends into (e.g., at least partially through) joined perimeter 36 (or between upper sheet 32 and lower sheet 34) at first perimeter edge 50 (i.e., from exterior opening 67*a* to or toward interior opening 67*b*. In alternative embodiments, however, one or more tubular members 60 can extend through other perimeter edge(s), through upper container wall 32, and/or through lower container wall 34. Multiple tubular members 60 can be or have the same configurations or different configurations and can be used for a variety of different purposes.

As depicted in FIG. 2B, tubular member 60*a* has an interior surface 62 that bounds a fluid channel 64. Tubular member 60*a* also has an exterior opening 61*a* at a first end of fluid channel 64 and an interior opening 61*b* at an opposing second end of fluid channel 64. Tubular member 60*b* can be similarly configured. As depicted, interior opening 61*b* of fluid channel 64 is disposed at or adjacent to interior opening 67*b* of opening 66*a*. However, as depicted, for example, in FIG. 3, interior opening 61*b* of fluid channel 64 can also be disposed within or extend into compartment 22. Regardless of specific configuration, fluid channel 64 is in fluid communication with the compartment 22 by means of opening 66.

Returning to FIG. 2B, fluid channel 64 has a first diameter $D1$ and fluid channel 64 of tubular member 60*b* has a second diameter $D2$. In at least one embodiment, diameters $D1$ and $D2$ can be or have similar measurements. For instance diameters $D1$ and $D2$ can be substantially the same. Alternatively, diameter $D1$ can be greater than diameter $D2$, or vice versa. Diameters $D1$ and $D2$ can also have any suitable size or measurement. In certain embodiments, however, diameters $D1$ and $D2$ are sized to induce and/or ensure a specific flow rate of fluid therethrough (e.g., in response to a specific pump pressure or speed). For instance, in specific embodiments diameters $D1$ and $D2$ can be at least, up to, greater than, less than, between, or about 1 mm, 2 mm, 2.5 mm, 3 mm, 4 mm, 5 mm, 7.5 mm, 10 mm, 15 mm, 20 mm, and so forth, including any diameter or range of diameters therebetween. Openings 66*a*, 66*b* can also have (fluid passageways having) diameter(s) sized as described in relation to channel 64.

Tubular member 60 can also have any suitable length (i.e., between exterior opening 61*a* and interior opening 61*b*. As depicted in FIG. 2B, tubular member 60 comprises a connection component, such as a port or adapter having a (relatively short) length of less than about 25 cm, 20 cm, 15 cm, 10 cm, 5 cm, or less. In other embodiments, however, tubular member 60 can be or comprise a fluid line or tube having a (relatively long) length of greater than 10 cm, 25 cm, 50 cm, 75 cm, 100 cm, 150 cm, 200 cm, 250 cm, 300 cm, or longer. In such an embodiment, exterior end 61*a* can be (sterilely) connected to a fluid source such as a second container (as discussed in further detail below). Thus, tubular member 60 depicted in FIG. 2B represents tubular members of any suitable length.

Figure 8:
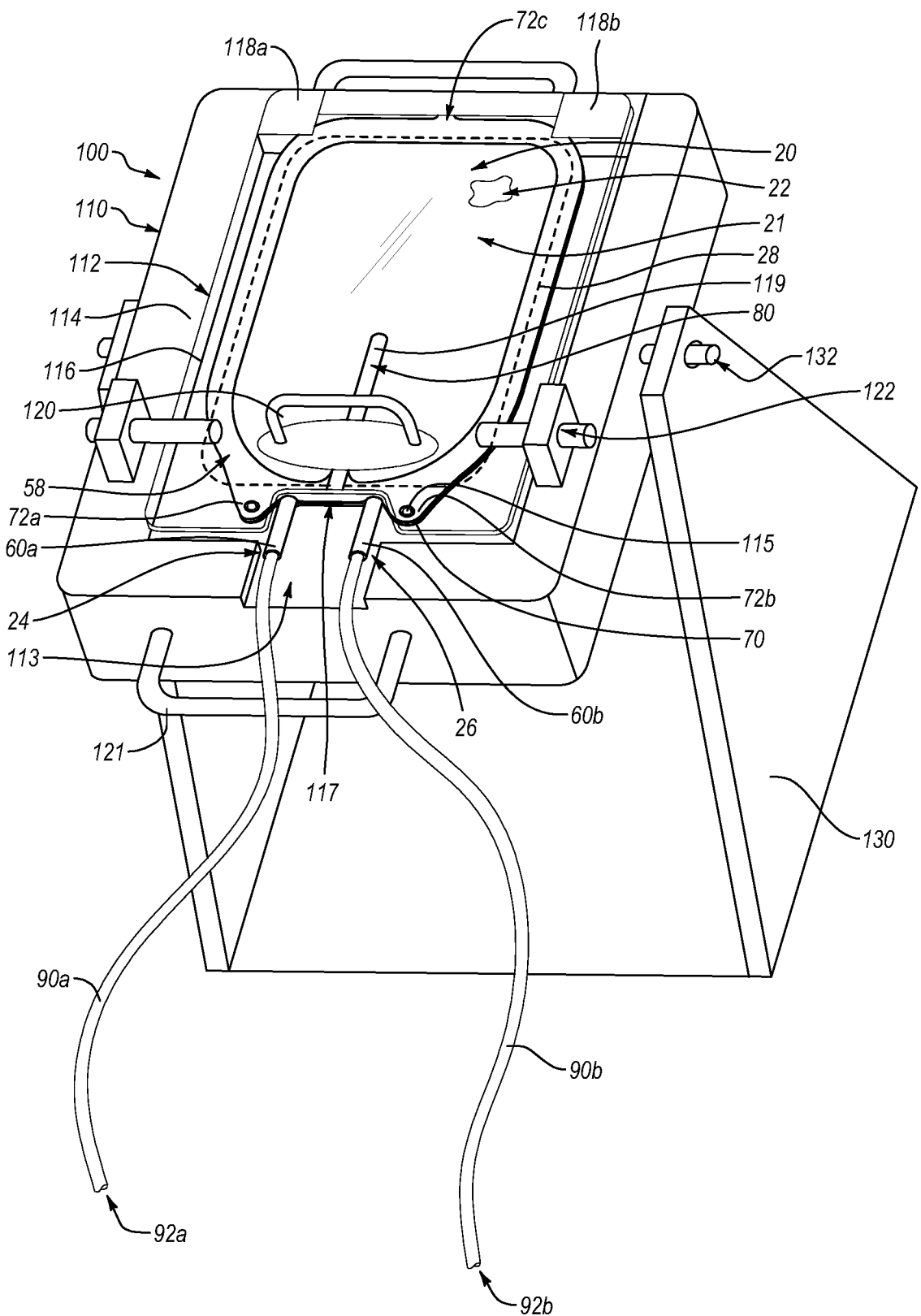
FIG. 8 is a particle separation assembly according to an embodiment of the present disclosure.

As depicted in FIG. 8, in some embodiments, tubular member 60 comprises the aforementioned connection component and has a fluid line 90 coupled thereto. A first fluid line 90a is coupled with and/or welded to tubular member 60a and a second fluid line 90b is coupled with and/or welded to tubular member 60b. As indicated above, however, it will be appreciated that tubular member 60 can be or comprise fluid line 90 and can, therefore, be connected (directly) to container 21 (i.e., without an intervening tubular member or connection component).

With continued reference to FIG. 8, fluid line(s) 90a, 90b can be of any suitable length and can have a fluid conduit 92a, 92b extending therethrough. Where fluid line 90 is coupled with tubular member 60, fluid conduit 92 can be in fluid communication with channel 64 and, therefore, in fluid communication with internal compartment 22. Fluid conduit(s) 92 can also have diameter(s) sized as described above in relation to opening 66 and channel 64. As indicated above, fluid channel 64 is in fluid communication with compartment 22.

In certain embodiments, tubular member 60 can be integrally formed with fluid line 90 for (sterilely) delivering media, cell cultures, and/or other components into and out of container 21 or compartment 22 thereof. Thus, fluid line(s) 90 can also be sterilizable (e.g., simultaneously with container 21) such as by ionizing radiation.

Examples of tubular member 60 and how various fluid lines can be coupled to containers is disclosed in United States Patent Publication No. 2006-0270036, published Nov. 30, 2006 and United States Patent Publication No. 2006-0240546, published Oct. 26, 2006, which are incorporated herein by specific reference.

In the embodiment depicted in FIGS. 2A and 2B, tubular members 60 (or interior opening 61b thereof) do not extend (substantially) from perimeter 36 into internal compartment 22. FIG. 3, however, depicts an alternative container assembly 20a comprising a container 21a with a first alternative tubular member 60c that extends a first length L1 into compartment 22 and a second alternative tubular member 60d that extends a second length L2 into compartment 22. Alternative tubular members 60c, 60d also comprise an interior (compartment) opening 61c disposed within compartment 22. Accordingly, opening 61c is not disposed at or in perimeter 36 or lower perimeter edge 50 thereof (adjacent to interior opening 67b as depicted in FIG. 2B). Instead, opening 61c is disposed length L1 away from perimeter 36, lower perimeter edge 50, and/or inner perimeter edge 37 thereof.

Lengths L1 and L2 can be or have similar measurements. For instance, lengths L1 and L2 can be substantially the same. Alternatively, length L1 can be greater than length L2, or vice versa. In certain embodiments, length L1 and/or L2 can be greater than 1 mm, 2 mm, 3 mm, 4 mm, 5 mm, and so forth. For instance, length L1 and/or L2 can be between about 1 mm and about 10 cm, preferably between about 1 mm and about 5 cm, more preferably between about 1 mm and about 2.5 mm.

Figure 6:
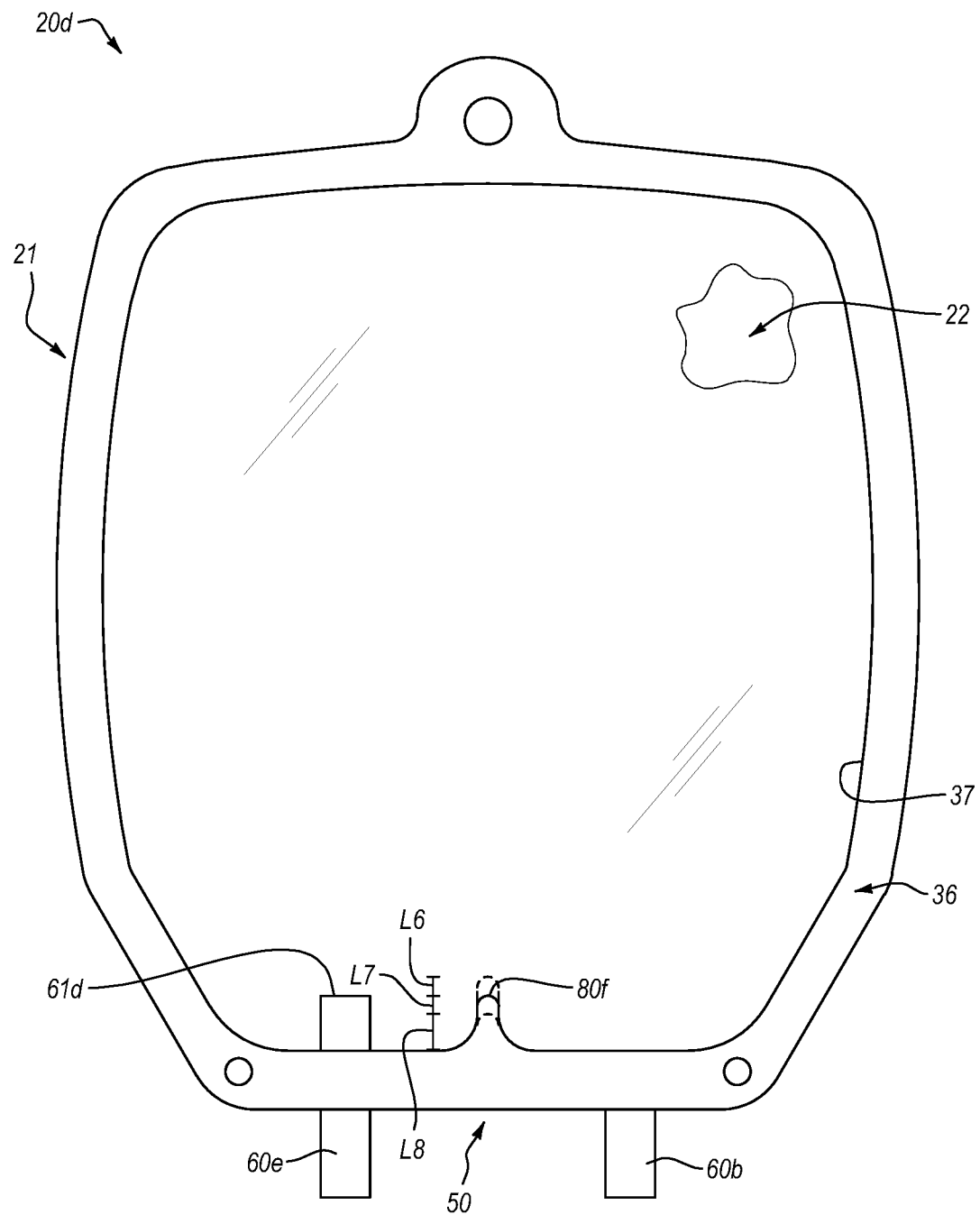
FIG. 6 is a top plan view of a container assembly according to still another embodiment of the present disclosure.
Figure 7:
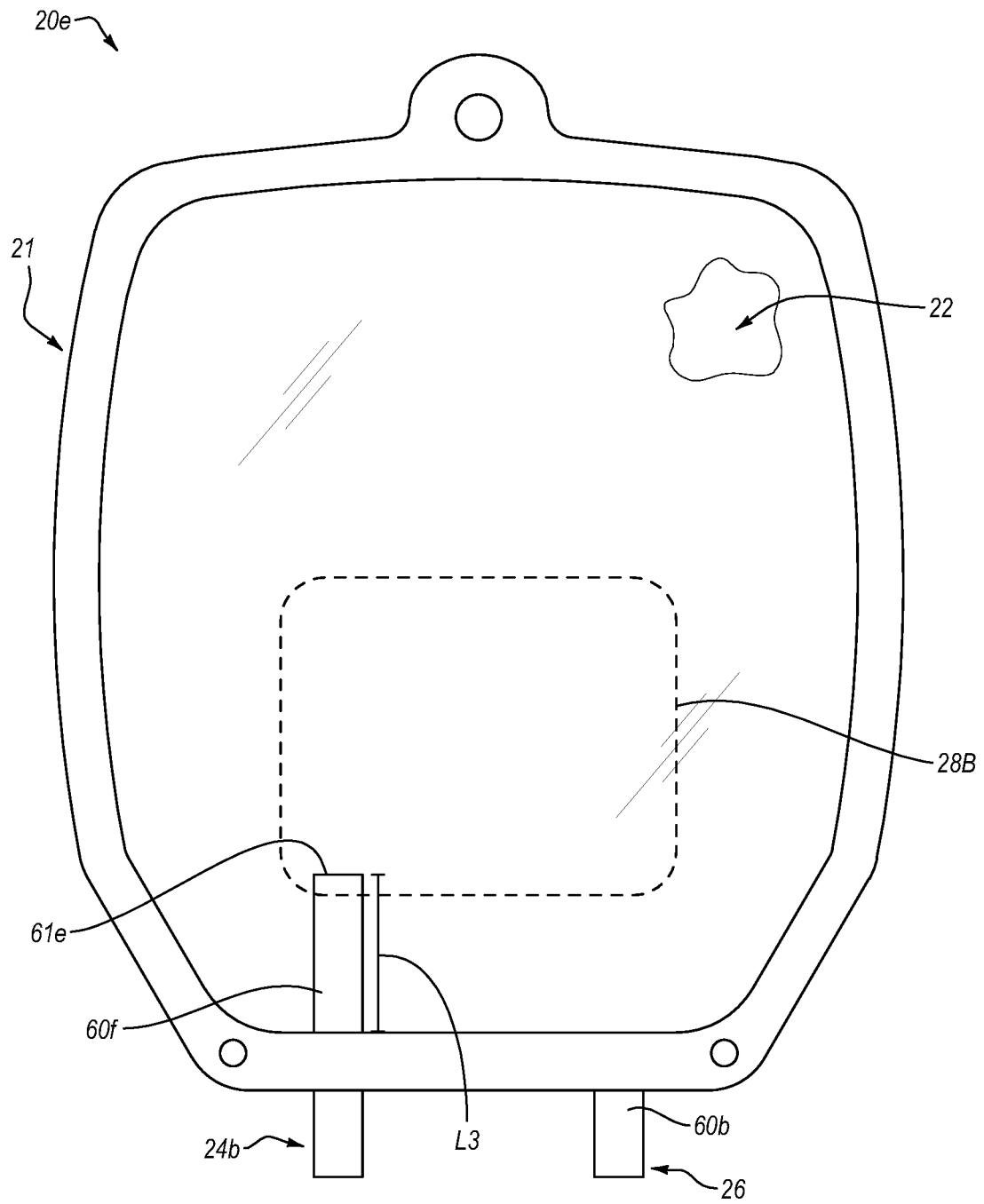
FIG. 7 is a top plan view of a container assembly according to still another embodiment of the present disclosure.

As further depicted in FIG. 6, certain embodiments can include one tubular member 60b (that does not extend (substantially) from perimeter 36 into internal compartment 22) and one tubular member 60e (that extends from perimeter 36 into internal compartment 22). FIG. 7 illustrates another alternative embodiment having one tubular member 60b an opposing tubular member 60f. Tubular member 60f extends a third length L3 into compartment 22. Third length L3 can be even longer that lengths L1, L2.

Partitions

Returning now to FIGS. 2A and 2B, container assembly 20 also includes partition 80 formed and/or disposed within internal compartment 22 (as indicated above). In particular, partition 80 extends from perimeter 36 (or inner edge 37 (of lower perimeter edge 50) thereof) into internal compartment 22 (e.g., toward inner edge 37 of upper perimeter edge 52). In certain embodiments, partition 80 comprises a joinder of opposing sides of interior surface 42 of wall 27. In particular, partition 80 comprises a joinder of upper container wall 32 and lower container wall 34 (or interior surface(s) 42 thereof). Partition 80 can be disposed at least partially between fluid inlet 24 and fluid outlet 26. For instance, partition 80 can extend from a first location disposed between and proximal to inlet 24 and outlet 26, to a second location within the internal compartment distal to inlet 24 and outlet 26.

In at least one embodiment, partition 80 has a (sealed) first end 82 connected to and/or extending from a first location at (perimeter 36 or lower perimeter edge 50 thereof at) first side 51 of container 21. Partition 80 also has a second end 84 opposite first end 82 disposed at a second location within compartment 22. The first location is disposed between and proximal to inlet 24 and outlet 26 (or first opening 66a and second opening 66b thereof) and the second location is distal to inlet 24 and outlet 26 (or first opening 66a and second opening 66b thereof). Accordingly, partition 80 extends (from perimeter 36) beyond first opening 66a and second opening 66b a first distance or length L4 into internal compartment 22.

Illustrated in dashed lines are representations of various alternative lengths for partition 80. For instance, in an alternative embodiment, partition 80 can extend (from perimeter 36) beyond first opening 66a and second opening 66b a second distance or length L5, or a third distance or length L6, into internal compartment 22. As discussed in further detail below, in certain embodiments, distance or length L4, L5, L6 of partition 80 can be above a certain minimum threshold (e.g., in order to force a fluid into an inner or non-peripheral area of compartment 22). For instance, distance or length L4, L5, L6 can be at least, greater than, or about the same as diameter D1 of channel 64 (or opening 66), or (between) half of diameter D1, twice diameter D1, or 3, 4, 5, 10, 50, or 100 times diameter D1. Distance or length L4, L5, L6 can also, or alternatively, be up to, at least, greater than, or about one-twentieth the distance between inner perimeter edge 37 of lower perimeter edge 50 and inner perimeter edge 37 of upper perimeter edge 52, or one-tenth, one-fifth, one-fourth, one-third, one-half, or two-thirds the distance between inner perimeter edge 37 of lower perimeter edge 50 and inner perimeter edge 37 of upper perimeter edge 52.

As depicted, partition 80 does not extend (all the way) from inner perimeter edge 37 of lower perimeter edge 50 to inner perimeter edge 37 of upper perimeter edge 52 (or other portion(s) of perimeter 36). Accordingly, distance or length L4, L5, L6 of partition 80 can also be limited below a certain maximum threshold. For instance, distance or length L4, L5, L6 can up to, less than, between, or about 10 times, 50 times, 100 times, 150 times, 200 times, 250 times, 300 times or 350 times diameter D1 of channel 64 (or opening 66). Distance or length L4, L5, L6 can also, or alternatively, be up to, less than, between, or about one-fifth, one-fourth, one-third, one-half, two-thirds, three-fourths, or seven-eighths the distance between inner perimeter edge 37 of lower perimeter edge 50 and inner perimeter edge 37 of upper perimeter edge 52. In at least one embodiment, distance or length L4, L5, L6 can be (between) about 2.5 mm, 5 mm, 10 mm, 20 mm, 40 mm, 50 mm, 60 mm, 65 mm, 70 mm, 75 mm, 80 mm, 100 mm, 150 mm, 163 mm, 165 mm, 175 mm, or 200 mm, including any distance or length or range of distances or lengths therebetween.

As discussed in further detail below, the distance or length L4, L5, L6 that partition 80 extends into compartment 22 and/or away from opening 66, perimeter 36, lower perimeter edge 50, and/or inner perimeter edge 37 thereof can at least partially determined the efficacy (i.e., the ability or capacity to produce a desired effect or result), effectiveness (i.e., the degree of success in producing the desired effect or result), and/or efficiency (i.e., producing the desired effect or result with minimal waste, expense, or unnecessary effort) of container assembly 20 in operation and/or when implemented in a method of separating magnetic particles from a fluid.

As indicated above, in at least one embodiment, partition 80 can be formed by (permanently or reversibly) joining (i.e., securing) together upper and lower walls 32, 34 of container 21 (e.g., between the inlet 24 and the outlet 26). In certain embodiments, joining the upper and lower walls 32, 34 can include (substantially irreversibly) bonding the walls together, such as by welding, adhering, etc. (e.g., in substantially the same way that perimeter 36 is seamed together). In other embodiments, joining the upper and lower walls together can include (reversibly) joining walls 32, 34, such as by (externally) pressing, pinching, etc. walls 32, 34 together. In further embodiments, joining the upper and lower walls together can include disposing a dividing element, such as a (polymeric) barrier member, between and/or to walls 32, 34 and/or within the compartment. Regardless of the specific configuration, partition 80 can restrict (linear and/or substantially direct) fluid communication between inlet 24 and outlet 36. Accordingly, it will be appreciated that (fluid) material (e.g., liquid media, biological component, magnetic particles, etc.) disposed within compartment 22 cannot pass through partitions 80. Instead, as discussed in further detail below, a fluid disposed in compartment 22 (and/or flowing into container 21 through inlet 24) must pass (or flow) around (the second end 84 of) partition 80 in order to exit container 21 (or internal compartment 22 thereof) through outlet 26, as direct, linear access between fluid inlet 24 (or first opening 66a thereof) and fluid outlet 26 (or second opening 66b thereof) is restricted by partition 80.

As a result of partition 80, compartment 22 has or forms a fluid pathway 23 that extends from inlet 24 (or opening 66 thereof), around second end 84 of partition 80, to outlet 26 (or opening 66b thereto). The extended length of fluid pathway 23 can increase the retention or residence time of fluid within compartment 22 as compared to bag 10 that does not include a partition. As discussed in further detail below, this increased residence time induces and/or increases exposure of magnetic particles disposed in the fluid to a magnetic field 28 applied and/or generated (so as to be disposed or positioned) at least partially within compartment 22. As depicted in FIG. 2A, at least a portion of magnetic field 28 can extend beyond compartment 22 in some embodiments. Indeed, various embodiments include magnetic fields of a suitable size, shape, surface area, etc.

FIG. 3 depicts an alternative partition 80a comprising a stem 86 (extending from perimeter 36 or lower perimeter edge 50 thereof, into compartment 22) and a capping element 87 disposed at second end 84a of partition 80a or stem 86 thereof. In at least some embodiments, partition 80a extends into compartment 22 a predetermined and/or suitable distance (as described previously) beyond opening 61c. Capping element 87 comprises opposing stem extensions (or fingers) 88a and 88b that, as depicted, extend (substantially) perpendicularly from second end 84a of partition 80a or stem 86 thereof. In alternative embodiments, however, fingers 88 can extend from an intermediate portion of partition 80a or stem 86 thereof and/or at any suitable angle. In further embodiments, capping element 87 (and/or stem 86) can comprise a body having any suitable shape (e.g., rectangular, square, rounded (i.e., circular, oval, oblong, etc.), triangular (or inverse triangular), rhomboidal, polygonal, and so forth.

Figure 4:
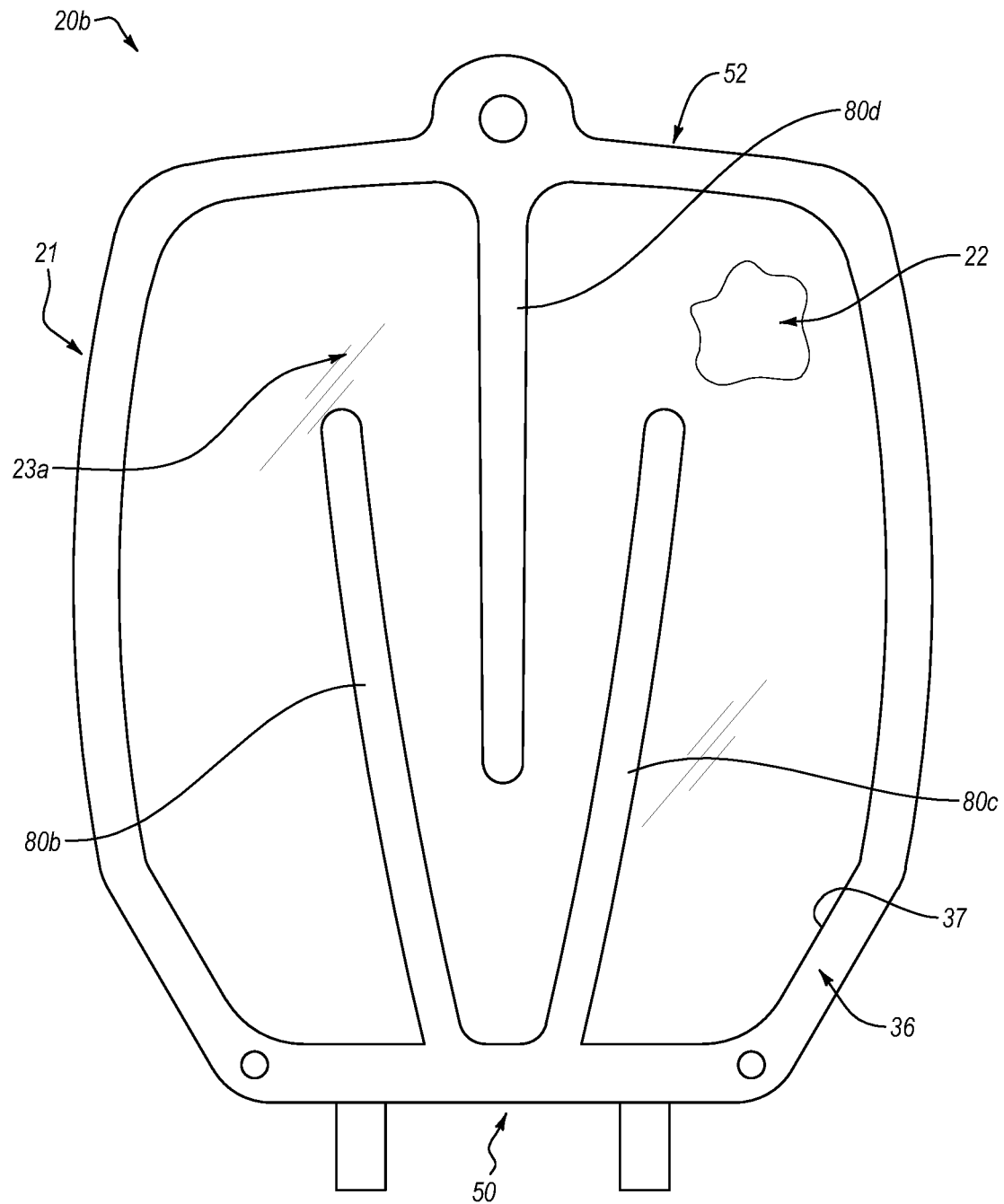
FIG. 4 is a top plan view of a container assembly according to yet another embodiment of the present disclosure.

Various additional partitions can be placed in a variety of different locations to form a variety of different flow paths. For instance, FIG. 4 depicts an alternative container assembly 20b comprising container 21, but with a plurality of partitions 80 formed therein. A first partition 80b and a second partition 80c extend from (inner edge 37 of) lower perimeter edge 50 of perimeter 36 (in a substantially V-shaped configuration). A third partition 80d extends from (inner edge 37 of) upper perimeter edge 52 of perimeter 36 (between first partition 80b and second partition 80c). Accordingly, partitions 80 of container assembly 20b form a serpentine or tortious fluid pathway 23a within container 21.

Figure 5:
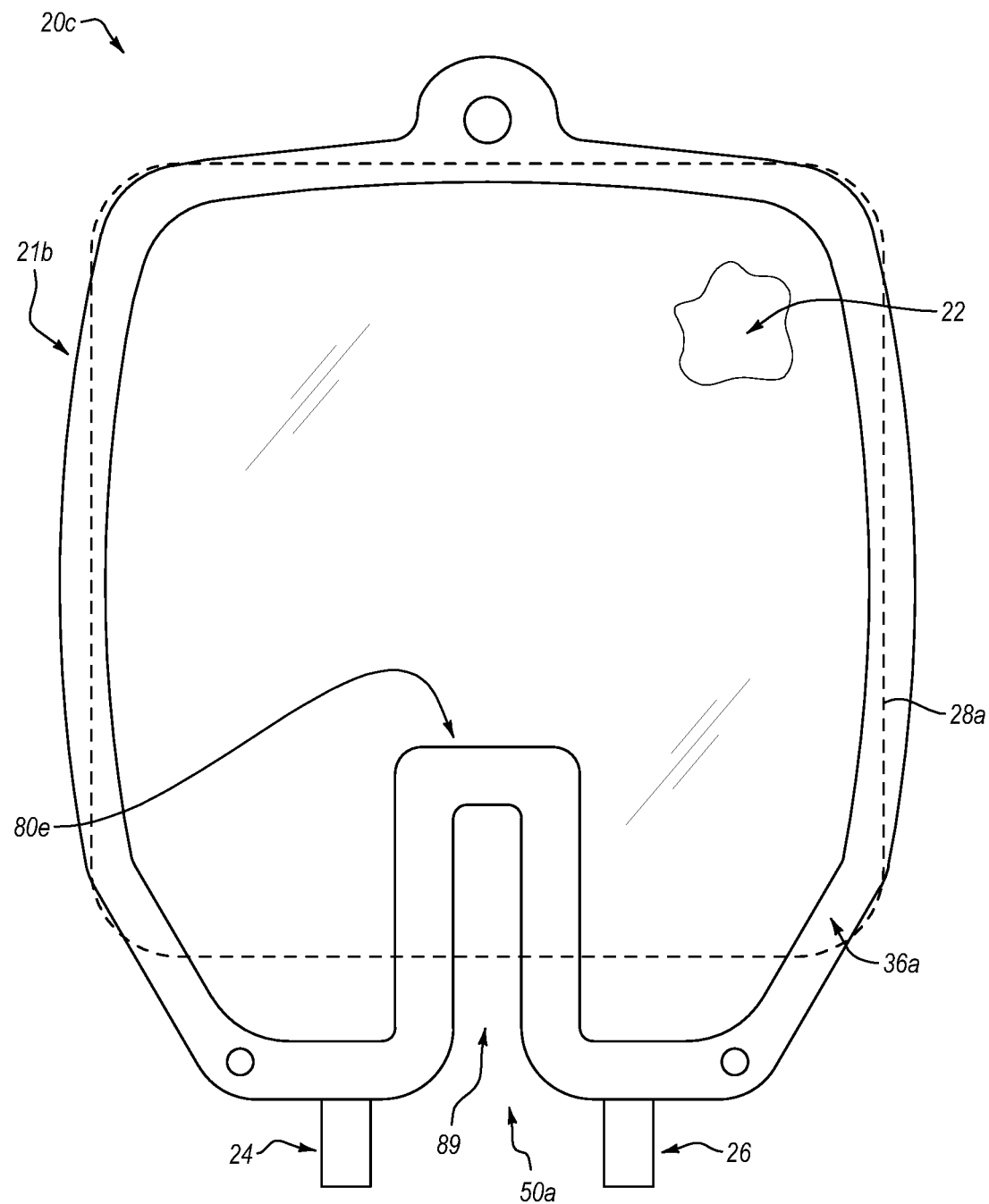
FIG. 5 is a top plan view of a container assembly according to still another embodiment of the present disclosure.

FIG. 5 depicts an alternative container assembly 20c comprising an alternative container 21b. Unlike container 21 and 21a, container 21b comprises a perimeter 36a having a lower perimeter edge 50a. Lower perimeter edge 50a extends into compartment 22 of container 21b to form a partition 80e. Partition 80e can function substantially similar to other partitions 80 described herein. However, partition 80e can occupy, remove, and/or eliminate a (substantial) portion of internal compartment 22 (e.g., between inlet 24 and outlet 26). In particular, partition 80e forms a gap or void 89 in the structural configuration of container 21b.

It will further be appreciated that further modification of container assembly 20c can result in a substantially and/or inverse U-shaped container 21b. Those skilled in the art will appreciate, however, that the U-shaped configuration of lower perimeter edge 50a can comprise and/or form partition 80e regardless of its size, shape, etc. Accordingly, a fluid passing into internal compartment 22 through inlet 24 of container 21b must pass around partition 80e, through magnetic field 28a, in order to pass out of internal compartment 22 through outlet 26. As depicted in FIG. 5, magnetic field 28a need be applied and/or generated (so as to be disposed or positioned) entirely within compartment 22. For instance, magnetic field 28a does not extend to lower perimeter edge 50a.

FIG. 6 depicts another alternative container assembly 20d. Unlike previously described container assemblies, container assembly 20d includes an alternative partition 80f. Partition 80f also extends from perimeter 36, lower perimeter edge 50, and/or inner perimeter edge 37 thereof, but does not extend substantially beyond an interior opening 61d (of tubular member 60e). Accordingly, partition 80f need not (necessarily and/or always) extend from perimeter 36 into internal compartment 22 beyond an opening 61. For instance, partition 80f can extend a length L7 (from perimeter 36 up to opening 61d). Illustrated in dashed lines are representations of alternative lengths for partition 80f. Partition 80f can alternatively extend a length L8 (from perimeter 36 but not as far as opening 61d extends into internal compartment 22). It will further be appreciated, however, that partition 80f can extend length L6 (beyond opening 61d and/or tubular member 60e) in certain embodiments.

FIG. 7 depicts yet another alternative container assembly 20e. Container assembly 20e does not include a partition 80. However, a tubular member 60f and/or an opening 61e thereof extends into compartment 22 a third distance or length L3. In certain embodiments, third distance or length L3 can be large enough so as to introduce a material (e.g., fluid) passing (e.g., flowing) therethrough directly into a magnetic field 28b. Accordingly, a fluid passing into internal compartment 22 through inlet 24b (and/or tubular member 60f thereof), must pass through magnetic field 28b in order to pass out of internal compartment 22 through outlet 26 (and/or tubular member 60b thereof). As depicted in FIG. 7, magnetic field 28b can be applied and/or generated (so as to be disposed or positioned) entirely within compartment 22 and/or such that magnetic field 28b does not (entirely) fill compartment 22.

FIG. 8 depicts a magnetic particle separation assembly 100 incorporating features of the present disclosure. Separation assembly 100 and/or operation thereof can be useful in implemented a method of separating magnetic particles from a fluid. In general, separation assembly 100 comprises a magnetic field generating device 110 and a container assembly 20 disposed on or in (at least a portion of) device 110.

Container assembly 20 can comprise and/or include any of the features described in relation to container assemblies disclosed herein. For instance, container assembly 20 includes container 21 having an internal compartment 22 and a partition 80 extending into compartment 22. Container assembly 20 also includes inlet tubular member 60a connected to fluid line 90a and outlet tubular member 60b connected to fluid line 90b, in fluid communication with compartment 22, and securing tabs 72a, 72b, and 72c.

Device 110 comprises an upper surface 114 and a receiving area 112. At least a portion of container assembly 20 and/or container 21 thereof is disposed on upper surface 114 and/or in receiving area 112. In one or more embodiments, receiving area 112 can be recessed into upper surface 114 of device 110. Accordingly, container 112 can be disposed and/or retained within the recess. Device 110 can also include one or more securing members 115 for receiving opening(s) 70 (e.g., to retain container 21 in a substantially constant and/or unchanged position or configuration on upper surface 114.

In at least one embodiment, device 110, upper surface 114, and/or receiving area 112 also comprises a recess (or (recessed) passage 113). Recess 113 can be positioned and/or configured to receive tubular member 60a and 60b therein (or allow tubular members 60 to pass therethrough without being structurally compromised. In particular, recess 113 can communicate with the recessed upper surface 114 and/or receiving area 112.

Device 110 also includes a magnetic field generating element 108 (FIG. 9) disposed beneath upper surface 114 of receiving area 112. The magnetic field generating element produces and/or is configured to produce (and position or disposed) magnetic field 28 above upper surface 114. In at least one embodiment, magnetic field 28 can have an area approximately the size of receiving area 112. For instance, magnetic field 28 can fill compartment 22 in certain embodiments.

Device 110 also comprises a lid 116. Lid 116 can be (hingedly) connected to receiving area 112 in some embodiments. For instance, lid 116 can be connected to receiving area 112 with and/or by means of one or more hinge elements 118a, 118b. Lid 116 also includes a handle 124 actuating lid 116 into an opened configuration such that container 112 can be placed in receiving area 112 and/or on upper surface 114 thereof. Lid 116 can be retained in a closed configuration (as depicted in FIG. 8) by means of one or more retention elements 122. In the closed configuration, lid 116 and receiving area 112 (and/or upper surface 114 thereof) can retain container 21 in a substantially flat and/or two-dimensional configuration. Lid 116 can also prevent opening(s) 70 from becoming separated from securing member(s) 115.

In at least one embodiment, lid 116 can include a partition rib 119 (overlaying partition 80) extending from the inside surface of lid 116 (adjacent receiving area 112 or upper surface 114. In such embodiments, partition rib 119 can press together the opposing polymeric sheets of container 21 so as to form partition 80 within compartment 22. In particular, upper sheet 32 and lower sheet 34 can be secured (e.g., pinched or sandwiched) between (recessed) upper surface 114 and partition rib 119 such that a (substantially) fluid- or liquid-tight seal is formed between the opposing polymeric sheets (e.g., along the length of the partition rib 119). Accordingly, liquid within compartment 22 flows around partition 80 formed by the pinching of upper sheet 32 and lower sheet 34 between (recessed) upper surface 114 and partition rib 119.

Partition rib 119 can have a length as described above in relation to partition 80. Moreover, partition 80 can have a length corresponding to (at least a portion of) the length of partition rib 119. Partition rib 119 can also be positioned on the inner surface of lid 116 so as to avoid contacting, deforming, and/or interfering with the inlet 24, outlet 26, tubular members 60, and/or openings 66 thereof.

Assembly 100 also includes a base support 130. Device 110 can be hingedly connected to base support 130 by means of a hinge mechanism 132. Accordingly, device 110 can be disposed and/or maintained at an angle relative to base support 130 and/or a surface on which base 130 is placed. By way of illustration, handle 121 of device 110 can be actuated downward (e.g., toward base support 130 and/or a surface on which base 130 is placed) such that device 110 (and thereby container 21) is tilted downward.

Exemplary methods of separating magnetic particles from a fluid can be illustrated through the operation of assembly 100. It will be appreciated, however, that certain embodiments of the present disclosure can include methods that do not depend on and/or are not tied to one or more of the structural components of assembly 100. Accordingly, while a discussion of exemplary methods may be facilitated by reference to assembly 100, it is noted that components of assembly 100 as depicted in FIG. 8 are not intended to limit the scope of other methods of separating magnetic particles from a fluid.

Thus, by way of illustration only, one or more embodiments of the present disclosure can include introducing a fluid mixture into internal compartment 22 of a flexible container 21 through inlet 24, allowing at least a portion of the fluid mixture to travel around partition 80 and then exit internal compartment 22 through outlet 26, and applying magnetic field 28 to the fluid mixture in internal compartment 22. The fluid mixture can comprise a liquid media, a biological component, and magnetic particles in some embodiments. In some embodiments, the liquid media can comprise a cell culture media and the biological component can comprise cells (e.g., growing in the liquid media). For instance, in at least one embodiment, the fluid mixture comprises a suspension cell culture of cells (e.g., human T-cells disposed and growing in the liquid media. The magnetic particles can comprise inert and/or superparamagnetic beads having one or more antibodies (e.g., anti-CD3 and anti-CD28) coupled thereto. The beads can also have a substantially uniform diameter (e.g., about 4.5 µm) in some embodiments. In one or more embodiments, the beads (or antibodies thereof) can (immuno-) activate the cells for therapeutic functionality or purposes.

It will be appreciated that the method can also include disposing container assembly 20 (or container 21 thereof) on or in magnetic field-generating device 110, (recessed) upper surface 114, or (recessed) receiving area 112 thereof. In addition, openings 70 can be disposed on or about securing members 115, tubular members 60a, 60b can be disposed in passage 113, and/or lid 116 can be closed (e.g., against container 21 such that at least a portion of the container becomes flattened into a substantially two-dimensional configuration). Accordingly, container 21 can be (or become) sandwiched and/or otherwise disposed between (recessed) upper surface 114 (or receiving area 112) and closed lid 116. Lid 116 can also include a recessed portion 117 configured to accommodate (or avoid contact with) tubular members 60a, 60b in recess 113 (e.g., without deforming tubular members 60a, 60b so as to (substantially or entirely) restrict fluid flow therethrough).

Furthermore, fluid flowing into compartment 22 through inlet 24 (or inlet tubular member 60a thereof) may not (necessarily) fill compartment 22 so as to expand container 21 into a substantially three-dimensional configuration (e.g., because of the pillow style configuration of container 21 and/or the force of secured lid 116 against container 21).

In order to exit compartment 22, the fluid passes (or must pass) around partition 80 in order to reach outlet tubular member 60b. With container assembly 20 disposed on upper surface 114 or in receiving area 112, magnetic field 28 is also disposed and/or generated in compartment 22. Accordingly, a fluid flowing into compartment 22 through tubular member 60a, around partition 80, and out of compartment 22 through tubular member 60b, can pass (or must pass) through magnetic field 28.

In some embodiments, as indicated above, the length that partition 80 extends into compartment 22, etc. can at least partially determined the efficacy, effectiveness, and/or efficiency of container assembly 20 in operation and/or when implemented in a method of separating magnetic particles from a fluid (e.g., in assembly 100). In certain embodiments of the present disclosure, the length of partition 80 can be large enough and/or optimize to ensure that the magnetic particle-containing fluid can be exposed to magnetic field 28 to a degree sufficient to separate the magnetic particles from the fluid and/or other components disposed therein. For instance, in certain embodiments, the distance or length of partition 80 (e.g., from perimeter 36 and/or opening 66) is at least, greater than, or about the same as the diameter of opening 66, or (between) half of the diameter, twice the diameter, or 3, 4, 5, 10, 50, or 100 times the diameter of opening 66, including any length or range of lengths therebetween. The distance or length of partition 80 can also, or alternatively, be up to, at least, greater than, or about one-twentieth, one-tenth, one-fifth, one-fourth, one-third, one-half, or two-thirds the length of container 21 or compartment 22 thereof (e.g., between inner perimeter edge 37 of lower perimeter edge 50 and inner perimeter edge 37 of upper perimeter edge 52—see FIG. 2B), including any length or range of lengths therebetween.

Unlike existing systems that may require users to reduce the flow rate (e.g., below 30 mL/min, 20 mL/min, 15 mL/min, 10 mL/min, 5 mL/min, or 1 mL/min) in order to ensure a suitable exposure time to the magnetic field (see magnetic field 18 of FIG. 1), some embodiments of the present disclosure accommodate and/or permit increased flow rates through of a liquid sample through compartment 22. Such increased flow rates can reduce the operating time and/or allow for increased sample recovery in a given amount of time (relative to existing systems).

The fluid can also be introduced into compartment 22 at or above a fluid flow rate sufficient to permit the fluid to pass over and/or around partition 80. In at least one embodiment, the fluid can be introduced into container 21 or compartment 22 thereof (by means of fluid line 90a and inlet tubular member 60a) at of flow rate of at least, greater than, between, or about 10 mL/min, 20 mL/min, 30 mL/min, 50 mL/min, 100 mL/min, 150 mL/min, 200 mL/min, 250 mL/min, 300 mL/min, 350 mL/min, 400 mL/min, and so forth, including any flow rate or range of flow rates therebetween.

In addition, the fluid can be introduced into compartment 22 at (or below) a fluid flow rate (e.g., sufficient to permit the fluid to be exposed to magnetic field 28 for a suitable period of time). Specifically, in order to increase and/or sustain exposure of the fluid to magnetic field 28, the fluid flow rate may need to be maintained under a certain level. In at least one embodiment, the fluid can be introduced into container 21 or compartment 22 thereof (by means of fluid line 90a and inlet tubular member 60a) at of flow rate of up to, less than, between, or about 35 mL/min, 40 mL/min, 50 mL/min, 100 mL/min, 150 mL/min, 200 mL/min, 250 mL/min, 300 mL/min, 350 mL/min, 400 mL/min, 500 mL/min, 750 mL/min, 1 L/min, and so forth, including any flow rate or range of flow rates therebetween.

The magnetic particles can (thereby) be (or become) retained within container 21 and/or compartment 22 thereof by magnetic field 28 as the media and biological component flow from inlet 24, around partition 80, and to outlet 26. Accordingly, the portion of the mixture that exits internal compartment 22 can be substantially devoid of magnetic particles. For instance, the portion of the fluid mixture that exits internal compartment 22 through outlet 24 can have less than 5000, 4000, 3000, or 2000, preferably less than 1000, 750, 500, or 250, more preferably less than 200, 150, 100, or 50, most preferably less than 40, 30, 25, 20, 15, or 10 magnetic particles per milliliter of liquid media. Thus, in addition to the time savings produced by increasing the flow rate of fluid sample through compartment 22, embodiments of the present disclosure can retain more beads and/or a higher percentage of beads than certain existing containers.

The concentration of the biological component in the portion of the mixture that exits the internal compartment, however, can be substantially the same as the concentration of the biological component in the introduced fluid mixture in some embodiments. For instance, the concentration of the biological component in the portion of the mixture that exits the internal compartment can be at least, greater than, between, or about 80%, 85%, 90%, 95%, 96%, 97%, 98%, or 99% of the concentration of the biological component in the introduced fluid mixture. In other embodiments, the concentration of the biological component in the portion of the mixture that exits the internal compartment can be at least, greater than, between, or about 10%, 25%, 50%, 60%, 70%, or 75%, of the concentration of the biological component in the introduced fluid mixture. For instance, certain embodiments may involve flowing the sample through the system at a high flow rate, and recirculating the recovered product through the container.

With upper surface 114 oriented in certain non-perpendicular angles relative to the force of gravity (e.g., by means of hinge mechanism 132), the fluid can drain from compartment 22 through tubular member 60b under the (at least partial) assistance of gravity. However, in such an orientation, fluid flowing into compartment 22 through tubular member 60a must overcome the (at least partial) force of gravity in order to eclipse and/or pass over (i.e., flow around) partition 80. Failure of the fluid to eclipse and/or pass over (i.e., flow around) partition 80 (and/or reach outlet 26) can result in loss of the biological component (disposed in the liquid media).

In some embodiments, the biological component (e.g., human T-cells or other therapeutic component) can be fragile. Thus, squeezing or rolling container 21, or implementing a container scrapper to move the fluid over partition 80 and to outlet 26 can damage (e.g., rupture) the biological component. Such damage can reduce the potency and/or usability of the biological component. Moreover, the additional expense of man-hours required to manually harvest the biological component can add to the baseline cost of producing (e.g., growing, expanding, activating, etc.) and purifying the biological component can destroy and/or negate the commercial viability to large-scale purification of the biological component. Accordingly, efficacious, effective, and/or efficient separation of magnetic particles may only be one of a plurality of concerns in performing the steps of a method of separating magnetic particles from a fluid (e.g., in assembly 100).

Without being bound to any theory, the longer and/or further partition 80 extends into compartment 22, the longer magnetic beads can be exposed to magnetic field 28. However, longer partitions can trap biological component-containing liquid in the container, reducing recover of the biological component. Accordingly, in certain embodiments, the length of partition 80 can be optimized (e.g., above a certain minimum threshold and below a certain maximum threshold) in order to maximize and/or optimize the amount of fluid that reaches tubular member 60b and/or exits compartment 22 through outlet 26. For instance, in order to maximize product recovery and/or minimize additional recovery efforts, the size of partition 80 can be reduced below a certain length. In some embodiments, the length of partition 80 can be up to, less than, between, or about 10 times, 50 times, 100 times, 150 times, 200 times, 250 times, 300 times or 350 times diameter of opening 66, including any length or range of lengths therebetween.

In certain embodiments, the length of partition 80 can also, or alternatively, be up to, less than, between, or about one-fifth, one-fourth, one-third, one-half, two-thirds, three-fourths, or seven-eighths the length of container 21 or compartment 22 thereof (e.g., between inner perimeter edge 37 of lower perimeter edge 50 and inner perimeter edge 37 of upper perimeter edge 52—see FIG. 2B), including any length or range of lengths therebetween. In at least one embodiment, the length of partition 80 can be (between) about 2.5 mm, 5 mm, 10 mm, 20 mm, 40 mm, 50 mm, 60 mm, 65 mm, 70 mm, 75 mm, 80 mm, 100 mm, 150 mm, 163 mm, 165 mm, 175 mm, or 200 mm, including any length or range of lengths therebetween.

The shape of container 21 and/or compartment 22 thereof can also affect the ability or tendency of fluid to flow from inlet 24, around partition 80, and to outlet 26. Where device 110 (and thereby container 21) is tilted downward, as described above, the fluid introduced into compartment 22 through opening 66 can tend to settle downward (e.g., back towards inlet 24) under the force of gravity. In some embodiments, partition 80 can form (an undesirable) pocket(s) with perimeter 36 (e.g., in the lower portion of compartment 22). Just as the lower corners of container 21 or compartment 22 thereof can form a fluid retention pockets (e.g., eliminated by transition perimeter edges 58), the side and/or upper portions (e.g., upper corners) of container 21 or compartment 22 thereof can also retain fluid therein.

With reference to FIG. 2B, in some embodiments, transition perimeter edge(s) 58a, 58b can inhibit and/or substantially prevent fluid from collecting in such pocket(s) (e.g., at lower end 51 of container 21. For instance, transition perimeter edges 58a, 58b can occupy and/or be formed in a portion of the lower corner(s) of container 21. Thus, transition perimeter edges 58a, 58b can reduce the size, volume, area, etc. of lower container pocket(s) that may be filled with and/or trap the fluid that flows into compartment 22. In addition, as the fluid is introduced into compartment 22, transition perimeter edges 58a, 58b can direct the fluid up toward away from inlet tubular member 60a. The upward flow of the fluid can enhance the passage of the fluid over and/or around partition 80. Similar transition perimeter edges can also be disposed in the upper end 53 of container 21 and/or upper portion of compartment 22.

Figure 9:
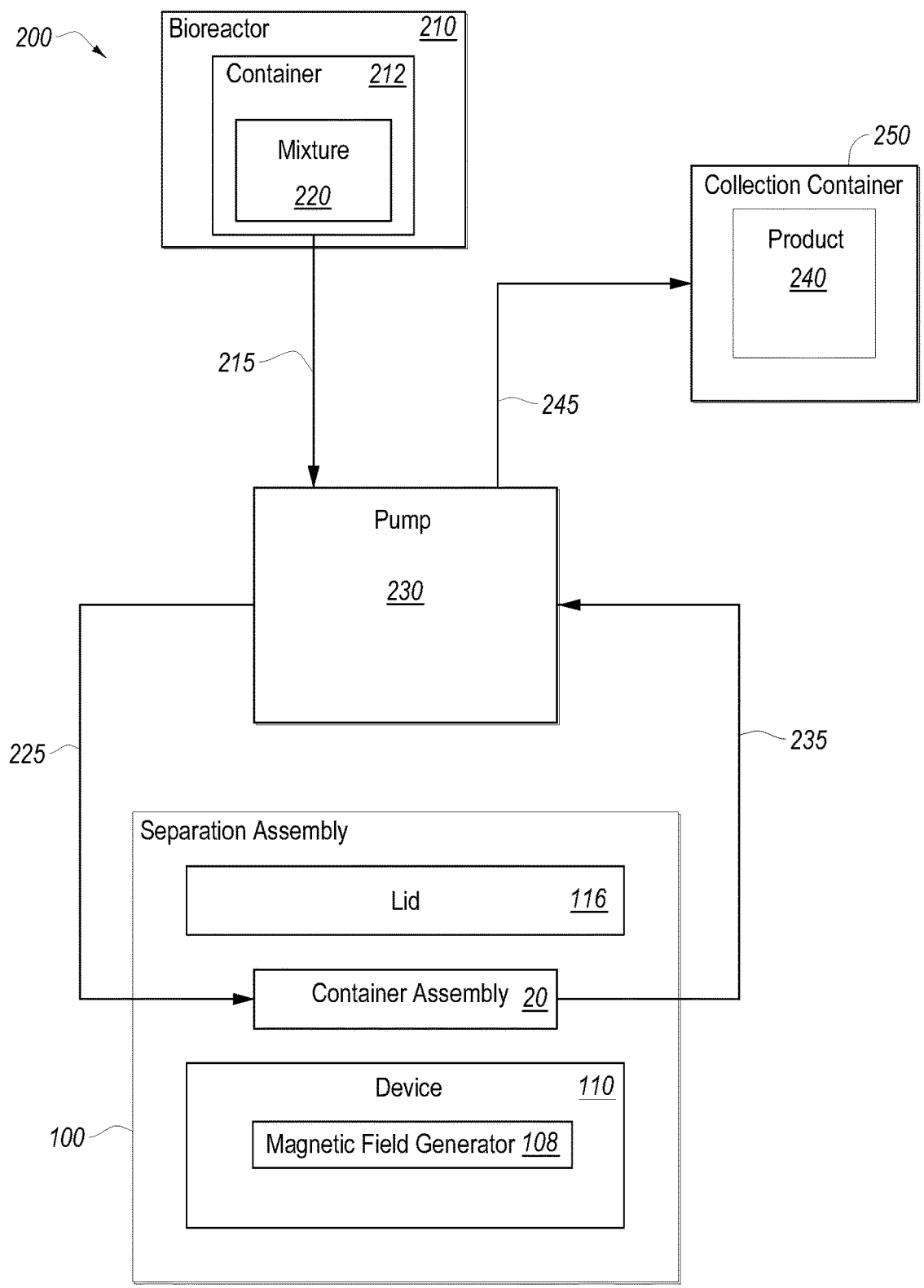
FIG. 9 is a schematic diagram depicting a particle separation system according to an embodiment of the present disclosure.

FIG. 9 depicts a schematic diagram of a magnetic particle separation system 200 incorporating features of the present disclosure. In particular, system 200 can include a biological component production assembly (e.g., bioreactor) 210 comprising a production container (e.g., flexible, sterilizable bioreactor bag) 212. A fluid mixture 220 comprising a liquid media and a biological component can be disposed within container 212. In some embodiments, fluid mixture 220 can be or comprise a suspension cell culture, wherein the biological component comprises cells (e.g., human T-cells) disposed and/or growing in the liquid media. In at least one embodiment, the fluid mixture can also comprise magnetic particles disposed in the liquid media.

System 200 can also include a pump 230 in fluid communication with container 212 via a first fluid line 215. Pump 230 can draw a fluid mixture 220 out of container 212 and, by means of a second fluid line 225, and pump fluid mixture 220 to assembly 100 (see FIG. 8). In particular, fluid mixture 220 can be pumped into container assembly 20 (or container 21 thereof) as described above. In at least one embodiment, second fluid line 225 can comprise or be coupled with fluid line 90a depicted in FIG. 8.

Pump 230 can also draw fluid from container assembly 20 (or container 21 thereof) through a third fluid line 235. In at least one embodiment, third fluid line 235 can comprise or be coupled with fluid line 90b depicted in FIG. 8. In one or more embodiments, the drawn fluid can comprise a fluid product 240, which can be pumped. As described above, the (purified and/or processed) fluid product 240 can comprise the liquid media and the biological component (in a concentration substantially similar to the concentration of the biological component pumped into container assembly 20 (or container 21 thereof) through second fluid line 225). However, the fluid product can be substantially devoid of the magnetic particles, as described above, in one or more embodiments.

In certain embodiments, pump 230 can re-cycle the fluid product through assembly 100 by means of second fluid line 225 and third fluid line 235. In other embodiments, however, the fluid product need not be re-cycled. Instead, the fluid product can be pumped into a collection container 250 via a fourth fluid line 245. Collection container 250 can also comprise a flexible, sterilizable bag in some embodiments.

Accordingly, with reference to the FIGS. 2B and 8-9, embodiments of the present disclosure can include and/or comprise introducing a first fluid mixture 220 into an internal compartment 22 of a flexible container 21 through a first opening 66a disposed in a first side 50 of the container 21, the container 21 comprising an upper container wall 32 and a lower container wall 34 joined at an encircling perimeter 36, the first opening 66a and the second opening 66b each comprising a tubular member 60 extending through the joined perimeter 36, at least a portion of the container 21 being disposed on or in a magnetic field-generating device 110, the device 110 producing a magnetic field 28 within at least a portion of the compartment 22, the first mixture 220 comprising a liquid media, a first amount of magnetic particles disposed in the liquid media, and a biological component disposed in the liquid media at a first concentration.

Embodiments can also include removing a second fluid mixture 240 from the compartment 22 through a second opening 66b disposed in the first side 50 of the container 21 adjacent to the first opening 66a, the second mixture 240 comprising the liquid media and the biological component disposed in the liquid media at a second concentration, the second concentration being greater than 90% of the first concentration, the magnetic field 28 retaining at least a portion of the first amount of magnetic particles in the compartment 22, the compartment 22 having a partition 80 formed therein, the partition 80 comprising a joinder of the upper container wall 32 and lower container wall 34, the partition 80 having a sealed first end 82 extending from the first side 50 of the container 21 between the first opening 66a and the second opening 66b, and a second end 84 opposite the first end 82 disposed at a second location within the compartment 22 such that the liquid media and the biological component must pass from the first opening 66a, around the partition 80, and to the second opening 66b in order to be removed from the compartment 22, the second fluid 240 comprising less than 5000 magnetic particles per milliliter of liquid media.

Various alterations and/or modifications of the inventive features illustrated herein, and additional applications of the principles illustrated herein, which would occur to one skilled in the relevant art and having possession of this disclosure, can be made to the illustrated embodiments without departing from the spirit and scope of the invention as defined by the claims, and are to be considered within the scope of this disclosure. Thus, while various aspects and embodiments have been disclosed herein, other aspects and embodiments are contemplated. While a number of methods and components similar or equivalent to those described herein can be used to practice embodiments of the present disclosure, only certain components and methods are described herein.

It will also be appreciated that systems, processes, and/or products according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features without necessarily departing from the scope of the present disclosure. Moreover, unless a feature is described as requiring another feature in combination therewith, any feature herein may be combined with any other feature of a same or different embodiment disclosed herein. Furthermore, various well-known aspects of illustrative systems, processes, products, and the like are not described herein in particular detail in order to avoid obscuring aspects of the example embodiments. Such aspects are, however, also contemplated herein.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the methods, products, devices, and apparatus disclosed herein may be made without departing from the scope of the disclosure or of the invention, which is defined in the appended claims. All changes which come within the meaning and range of equivalency of the claims are to be embraced within their scope.

What is claimed is:

1. A method of separating magnetic particles from a fluid, the method comprising:
   introducing a fluid mixture into an internal compartment of a flexible container through an inlet of the container, the container having a perimeter that encircles the internal compartment, the perimeter including a front side and an opposing back side with the internal compartment disposed therebetween, the inlet being disposed on the front side, the fluid mixture comprising a liquid media, a biological component, and magnetic particles, the container being disposed on a magnetic field generating device which is supported by a base support;
   allowing at least a portion of the fluid mixture to travel around a partition formed within the internal compartment and then exit the internal compartment through an outlet disposed on the front side of the container, the partition projecting into the internal compartment from the front side between the inlet and the outlet;
   tilting the magnetic field generating device relative to the base support so that the magnetic field generating device and container are tilted at an angle relative to the base support; and
   applying a magnetic field to the fluid mixture in the internal compartment so that the magnetic particles become retained within the container by the magnetic field as the media and the biological component flow from the inlet, around the partition and to the outlet.

2. The method of claim 1, wherein the biological component comprises cells.

3. The method of claim 2, wherein the cells comprise activated and/or expanded human T-cells, the magnetic particles comprising inert, superparamagnetic beads having anti-CD3 and/or anti-CD28 antibodies coupled thereto.

4. The method of claim 2, wherein the fluid mixture comprises a suspension cell culture of the cells growing in the liquid media.

5. The method of claim 1, wherein the fluid mixture is introduced into the internal compartment at a flow rate greater than or equal to about 20-30 mL/min.

6. The method of claim 1, wherein the portion of the fluid mixture that exits the internal compartment through the outlet comprises less than 1000 of the magnetic particles per milliliter of the liquid media.

7. The method of claim 1, further comprising closing a lid of the magnetic field generating device against the container such that at least a portion of the container becomes flattened into a substantially two-dimensional configuration.

8. The method of claim 1, wherein the flexible container comprises an upper container wall and a lower container wall joined at the encircling perimeter, the partition comprising a joinder of the upper container wall and the lower container wall.

9. The method of claim 8, wherein the inlet and the outlet each extend through the joined upper container wall and lower container wall at the encircling perimeter.

10. The method of claim 8, wherein the partition comprises at least one weld between the upper container wall and the lower container wall.

11. The method of claim 8, further comprising forming the partition by reversibly pressing together the upper container wall and the lower container wall such that the media and the biological component flow around the partition.

12. The method of claim 1, wherein the partition extends from a first location disposed between and proximal to the inlet and the outlet, to a second location within the internal compartment, the second location being distal to the inlet and the outlet, the inlet comprising a first opening having a first diameter, the outlet comprising a second opening having a second diameter, the first opening and the second opening being in fluid communication with the internal compartment, the partition extending beyond at least the first opening a first distance into the internal compartment, the first distance being at least half the first diameter and less than 350 times the first diameter.

13. The method of claim 1, further comprising recycling the at least a portion of the fluid mixture exiting the outlet of the container back into the inlet of the container.

14. The method of claim 1, further comprising a second partition projecting into the compartment so as to extend toward the back side and a third partition projecting into the compartment from the back side toward the front side, at least a portion of the third partition being disposed between the partition and the second partition so that the partition, the second partition and the third partition bound a serpentine or tortious fluid pathway through which the at least a portion of the fluid mixture travels as the at least a portion of the fluid mixture travels within the compartment of the flexible container from the inlet to the outlet.

15. The method of claim 14, further comprising the at least a portion of the fluid mixture traveling around a terminal end of the partition, a terminal end of the second partition, and a terminal end of the third partition as the at least a portion of the fluid mixture travels within the compartment of the flexible container from the inlet to the outlet.

16. The method of claim 14, further comprising the second partition projecting from the front side and being spaced apart from the back side.

17. The method of claim 1, wherein the magnetic field generating device is connected to the base support by a hinge mechanism that enables the magnetic field generating device to be tilted at an angle relative to the base support.

18. The method of claim 1, wherein the magnetic field generating device comprises:
   an upper surface having a receiving area formed thereon, the container being disposed on the receiving area; and
   a magnetic field generating element disposed beneath the upper surface and the receiving area, the magnetic field generating element being configured to produce a magnetic field above the upper surface.

19. The method of claim 18, wherein the receiving area is recessed into the upper surface.

20. The method of claim 19, further comprising a passage recessed into the upper surface and extending from an edge of the upper surface to the recessed receiving area, a tubular member projecting from the inlet of the container being received within the passage.

21. The method of claim 18, further comprising a handle outwardly projecting from the magnetic field generating device.

22. The method of claim 18, further comprising disposing the container on the receiving area of the upper surface so that securing members projecting from the upper surface are received within openings formed on the container so as to retain the container on the upper surface.

* * * * *